US006921632B2

(12) United States Patent
Lim et al.

(10) Patent No.: US 6,921,632 B2
(45) Date of Patent: Jul. 26, 2005

(54) HUMAN EMBRYONIC STEM CELLS DERIVED FROM FROZEN-THAWED EMBRYO

(75) Inventors: Jin-Ho Lim, Seoul (KR); Se-Pill Park, Seoul (KR); Eun-Young Kim, Seoul (KR)

(73) Assignee: Maria Biotech Co., Ltd., Seoul (KR)

(*) Notice: Subject to any disclaimer, the term of this patent is extended or adjusted under 35 U.S.C. 154(b) by 236 days.

(21) Appl. No.: 09/944,448

(22) Filed: Aug. 30, 2001

(65) Prior Publication Data

US 2002/0045259 A1 Apr. 18, 2002

(30) Foreign Application Priority Data

| Aug. 30, 2000 | (KR) | 2000-50881 |
|---|---|---|
| Nov. 6, 2000 | (KR) | 2000-65629 |
| Mar. 10, 2001 | (KR) | 2001-12485 |

(51) Int. Cl.$^7$ .............. A01N 1/00; A01N 63/00; A01N 65/00; C12N 5/00; C12N 5/02
(52) U.S. Cl. ............... 435/1.1; 435/325; 435/405; 424/93.1
(58) Field of Search ............... 435/325, 405, 435/1, 2.2; 424/93.1; 800/21

(56) References Cited

U.S. PATENT DOCUMENTS

| 5,690,926 A | 11/1997 | Hogan |
| 5,843,780 A | 12/1998 | Thomson |
| 6,271,436 B1 * | 8/2001 | Piedrahita et al. .......... 800/21 |
| 2003/0157710 A1 * | 8/2003 | Nakatsuji et al. ........... 435/363 |

OTHER PUBLICATIONS

Fassler et al, JCB 128:979–988 (May 2004).*
Spielmann et al. J Ebryol Exp Morphol 60:255–269 (Dec. 1980).*
Stojkovic et al. Anim Reprod Sci 50(1–2):1–9 (Feb. 27, 1998).*
Kaufnmann et al. Fert. Steril (1995) 64:1125–1129.*
Menzo et al. Human Reproduction, (1992) 7:101–106.*
Rall et al. Nature (1985) 313:573–575.*
Thomson, J.A. et al. (1998), "Embryonic Stem Cell Lines Derived from Human Blastocysts" *Science 282*: 1145–114.
Gearhart, J. (1998), "New Potential for Human Embryonic Stem Cells" *Science 282*: 1061–1062.
Reubinoff, B.E. et al. (2000), "Embryonic Stem Cell Lines from Human Blastocysts: Somatic Differentiation in Vitro" *Nature Biotechnology 18*: 399–404.
Pera, M.F. et al. (2000), "Human Embryonic Stem Cells" *Journal of Cell Science 113*: 5–10.
Bronson, S.K. et al. (1996), "Single–Copy Transgenic Mice with Chosen–Site Integration" *Proc. Natl. Acad. Sci. USA 92*:9067–9072.
Thomson, J.A. et al. (1995), "Isolation of A Primate Embryonic Stem Cell Line" *Proc. Natl. Acad. Sci. USA 92*:7844–7848.

* cited by examiner

Primary Examiner—Joseph Woitach
(74) Attorney, Agent, or Firm—Dorsey & Whitney LLP; Richard F. Trecartin; Traci H. Ropp

(57) ABSTRACT

The invention covers a method for establishing undifferentiated human embryonic stem cells by thawing cryopreserved human embryos, preferably blastocyst stage embryos, and culturing at least a portion of the embryos on a medium capable of sustaining undifferentiated embryonic stem cells, to establish undifferentiated human embryonic stem cells.

12 Claims, 16 Drawing Sheets

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial
<220> FEATURE:
<223> OTHER INFORMATION: antisense primer

<400> SEQUENCE: 1
ccacatcggc ctgtgtatat                                          20

<210> SEQ ID NO 2
<211> LENGTH: 20
<212> TYPE: DNA
<213> ORGANISM: Artificial
<220> FEATURE:
<223> OTHER INFORMATION: sense primer

<400> SEQUENCE: 2
ctcctggagg gccaggaatc                                          20

<210> SEQ ID NO 3
<211> LENGTH: 20
<212> TYPE: DNA
<213> ORGANISM: Artificial
<220> FEATURE:
<223> OTHER INFORMATION: sense primer

<400> SEQUENCE: 3
atgcatgagt cagtgaacag                                          20
```

HUMAN EMBRYONIC STEM CELLS DERIVED FROM FROZEN-THAWED EMBRYO

FIELD OF THE INVENTION

The invention is generally directed to undifferentiated human embryonic stem cells derived from frozen-thawed human embryos and methods of cultivating and propagating such undifferentiated human embryonic stem cells. The present invention also relates to a method for differentiation of specific cells from the undifferentiated human embryonic stem cells derived from frozen-thawed human embryos.

BACKGROUND OF THE INVENTION

In nature, stem cells are undifferentiated cells, which are able to differentiate into various functional, mature cells ranging from neuronal cells to muscle cells. Embryonic stem (hereinafter "ES") cells are derived from the embryo and are pluripotent in nature. ES cells are able to differentiate into a particular cell, tissue or even an organ type depending on the types of stimulus they are subject to.

Development of mouse ES cells was reported in 1981 (Evans et al., *Nature* 292:151–156; Martin, *Proc. Natl. Acad. Sci. U.S.A.* 78:7634–7638) and was associated with work on mouse teratocarcinomas. Teratocarcinoma research developed widely in the 1970's and association with the background developmental capacity of the EC (embryonal carcinoma) stem cells led to work on EC cells as models for studies on mammalian cell, tissue and organ differentiation. However, EC cells are neoplastic and they necessarily contain chromosomal aberrations which make their ability to differentiate into various tissue types limited.

Teratocarcinomas can be induced ectopically with blastocyst grafts, and it was hypothesized that pluripotential cell lines could be developed directly from blastocysts instead of tumors. This was the reported development of mouse ES cells in 1981 separately by Martin and Evans et al. The results were stable diploid cell lines that were said to be able to generate every adult tissue type. Teratocarcinomas have also been reported to have been developed from primordial germ cells in mice and from ectopic transplantation of primordial germ cells. In 1992, Matsui et al. published a report on obtaining EG (embryonic germ) cells from mouse primordial germ cells (*Cell* 70:841–847). EG cells have a developmental capacity very similar to ES cells. As murine ES cells can differentiate into any humoral cell type, mouse ES cells can be used in vitro to study mechanisms which control differentiation of specific cells or tissues. Study of mouse ES cells provides understanding on general differentiation of mammalian cells and tissues, but differences in primate and mouse development and specific lineages limited the use of mouse ES cells as a model for human development.

Pluripotential cell lines have also been derived from testicular carcinomas (Andrews et al., 1984, *Lab. Invest.* 50:147–162), who reported the derivation of cloned cell lines from human teratocarcinoma which could differentiate in vitro into neurons and other cell types. Cell lines which could differentiate into tissues representative of all three embryonic germ layers were also developed (Pera et al., 1988, *Differentiation* 39:139–149). These studies on human cellular development showed that these derivations were aneuploid, of limited capacity for spontaneous differentiation into somatic tissue, and different from mouse ES or EC cell phenotype.

Development of primate ES cells from rhesus monkey and marmoset blastocysts have been published (Thomson et al., 1995, *Proc. Natl. Acad. Sci. U.S.A.* 92:7844–7844; 1996, *Biol. Reprod.* 55:254–259). Such primate cell lines were diploid, but they closely resembled human EC cells otherwise. These studies on monkey cells showed that work on primates including human EC cells are associated with pluripotent stem cells which are different in phenotype from mouse ES cells, and could be derived from a human blastocyst.

Short term culture and maintenance of cells from human embryos fertilized in vitro was reported by Bongso et al. in 1994 (*Hum. Reprod.* 9:2110–2117). The isolated cells had morphology expected of pluripotent stem cells, but these early studies did not employ feeder cell support, and it was impossible to achieve long term maintenance of the cultures. Thomson et al. (1998, *Science* 282:1145–1147) derived ES cells from human blastocyst by removing the trophectoderm by immunosurgery, then plating the inner cell mass onto a mouse embryonic fibroblast feeder cell layer, and following a brief period of attachment and expansion, the resulting outgrowth was disaggregated and replated onto another feeder cell layer. The phenotype of the resulting cells was similar to the human EC cells reported by Pera et al., supra.

Thomson et al.'s studies on primate ES cells showed no evidence that these cells had the capacity for somatic differentiation in vitro. The only evidence for in vitro differentiation was for limited expression of markers characteristic of trophoblast and endoderm formation such as human chorionic gonadotropin alphafetoprotein production. It is difficult to substantiate that cells which produce alphafetoprotein are equivalent to those which make up extraembryonic or embryonic endoderm.

A method for establishing ES cells by culturing undifferentiated primordial germ cells from miscarried fetus, which were 5 to 9 weeks old, has been described (Shamblott et al., 1998, *Proc. Natl. Acad. Sci. U.S.A.* 95:13726). However, the method did not provide either high quality ES cells or a method for differentiating ES cells derived from long-term stored, frozen embryos to specific cells.

Reubinoff et al., published an article regarding ES cells derived from relatively fresh blastocyst stage embryos, which were 6 days old after fertilization (2000, *Nature* 18:399–404). Reubinoff reports the propagation of undifferentiated human ES cells and production of human ES cells capable of yielding somatic differentiated cells. However, this method did not provide an efficient method for generating high quality ES cells derived from long-term stored, frozen embryos.

Human EC cells will form teratocarcinomas with derivatives of multiple embryonic lineages in tumors in nude mice. However, the range of differentiation of these human EC cells is limited compared to the range of differentiation obtained with mouse ES cells, and all EC cell lines derived are aneuploid (Andrews et al., 1987, supra). ES cells, on the other hand, are thought to retain greater developmental potential because they are derived from normal embryonic cells in vitro, without the selective pressures of the teratocarcinoma environment. True ES cells should: (i) be capable of indefinite proliferation in vitro in an undifferentiated state; (ii) maintain a normal karyotype through prolonged culture; and (iii) maintain the potential to differentiate to derivatives of all three embryonic germ layers (endoderm, mesoderm, and ectoderm) even after prolonged culture.

Any method that would allow production of human ES cells is desirable, since human ES cell lines would permit easier study of early human development, and the use of such human ES cell lines would enable the development of cell cultures for transplantation, manufacture of biopharmaceutical products, and development of biological-based sensors. Importantly, the ability to produce large quantities of human cells has important working applications for the production of substances, such as insulin or factor VIII which currently must be obtained from non-human sources or donors; implantation to treat diseases, such as Parkinson's diseases; tissue for grafting; and screens for drugs and toxins.

It is an objective of the present invention to overcome or at least alleviate some of the problems of the prior art and to provide a more effective and practical method for producing human ES cells, and the following disclosure provides a practical system which meets the needs in the art as described above and provides additional advantages as well.

SUMMARY OF THE INVENTION

The present invention relates to a method for establishing undifferentiated human embryonic stem (herein after "ES") cells and an undifferentiated human ES cell line formed therefrom.

In one aspect of the invention, a method for establishing undifferentiated human ES cells is provided and the method comprises the steps of thawing a cryopreserved human embryo, and culturing at least a portion of the embryo on a medium capable of sustaining undifferentiated embryonic stem cells.

In another aspect of the present invention, ES cells are derived from frozen-thawed human blastocyst stage embryo. The method comprises the steps of thawing a cryopreserved human blastocyst embryo and culturing at least a portion of said embryo on a medium capable of sustaining undifferentiated embryonic stem cells.

In another embodiment of the present invention, a method for establishing undifferentiated human ES cells is provided, which comprises the steps of obtaining a population of cryogenically stored human embryos in the blastocyst stage of development, thawing one or more of the embryos, and culturing at least a portion of each of the thawed embryos on a medium capable of sustaining undifferentiated ES cells.

In another aspect of the invention, a method for establishing undifferentiated human ES cells is characterized in that the method comprises the steps of thawing a cryopreserved human embryo in a solution comprising human follicular fluid (hereinafter "hFF") and successive steps of treating the thawed human embryo in two or more solutions comprising hFF and cryoprotectant.

In another aspect of the invention, the method further comprises a step of removing trophectoderm from the embryo using anti-human lymphocyte antibody. In the preferred method for establishing undifferentiated human ES cells, the portion of the embryo comprises the inner cell mass (hereinafter "ICM").

The present invention also relates to a method for isolating the ICM of a human blastocyst embryo comprising the steps of treating the embryo with an anti-human lymphocyte antibody. Preferably, the method for isolating the ICM further includes a human blastocyst embryo, which has been cryopreserved and thawed.

In another aspect of the invention, a method of differentiating human ES cells is provided and comprises the step of differentiating ES cells obtained in this process in a culture medium comprising growth factors.

These features will now be described with the aid of the accompanying drawings.

DETAILED DESCRIPTION OF THE INVENTION

Figure 1:
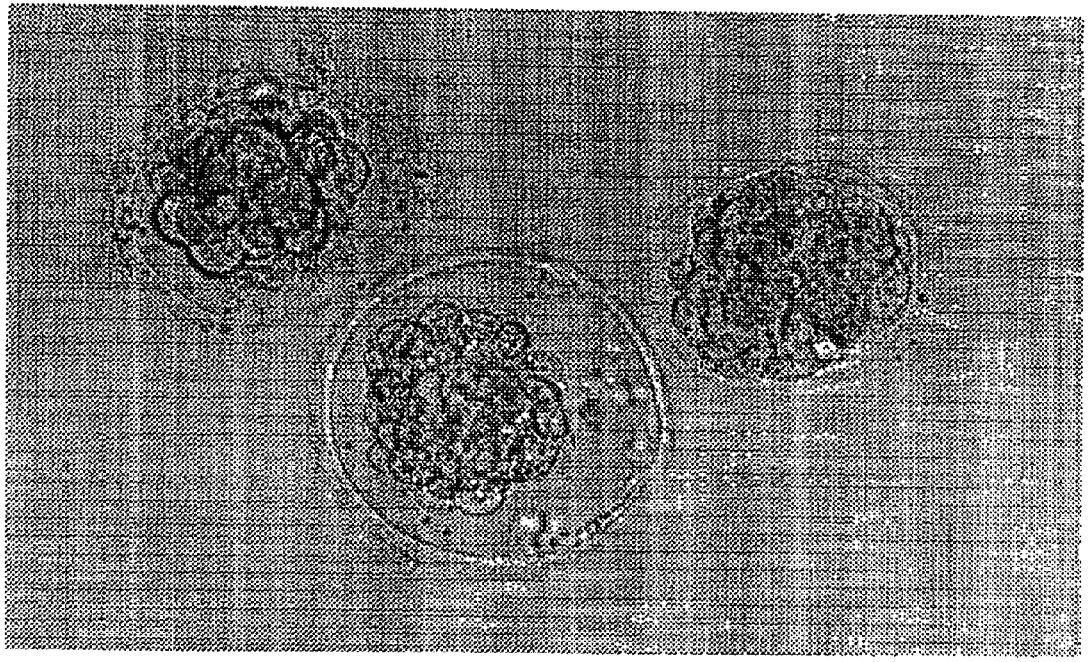
FIG. 1 is a microscopic photograph (X200) showing a thawed human embryo at the blastocyst stage. The embryo was cryopreserved prior to thawing.

The invention provides a method for establishing undifferentiated human embryonic stem (ES) cells from frozen-thawed embryo and an undifferentiated human ES cell line formed from such cells. In particular, the present invention provides a method for establishing undifferentiated human ES cells from frozen-thawed human blastocyst stage embryo.

The present invention further relates to a method for differentiating human ES cells into specific cells.

The development of ES cell cultures that can be maintained as cell lines permits investigation of fundamental questions regarding the biochemical and cellular properties of these cells and the dynamics of interaction in their cellular and chemical environment. In addition, useful tissues and substances can be produced using the human ES cells of the invention.

A key feature of the present invention is the use of a frozen-thawed embryo. Fresh fertilized eggs obtained from in vitro fertilization (IVF) have been used in most of the prior cases. Generally in infertility clinics, fertilized eggs are frozen and maintained in frozen state for future implantation, and, thus, it is hard to get permission from the patients for use of such eggs for research purposes. However, a characteristic feature of the present invention is to use fertilized eggs that are frozen for a certain period of time, preferably, fertilized eggs that are to be discarded after being cryogenically stored for many years without implantation. Therefore, the present invention permits a larger number of fertilized eggs to be utilized for ES cell formation because the invention uses frozen fertilized eggs that are no longer needed or are to be discarded. Further frozen fertilized eggs can still be utilized with the patient's permission even if they are not to be discarded. Furthermore, since unnecessary or to-be-discarded eggs can be used, such can be more freely used without having to address a variety of ethical issues. Therefore, the most advantageous feature of the present invention is to successfully derive ES cells from long-term stored frozen embryos, particularly those which are unnecessary or to be discarded.

Another feature of the present invention is use of a frozen blastocyst stage embryo. Large numbers of fertilized eggs (i.e., embryos) die in the early stages of egg development, particularly embryos at about 2 or 3 days or less after fertilization; this time period of embryo development typically includes the cleavage stages preceding and including the morula stage. Thus, the number of surviving embryos is very limited in the case of using 2–3 days old embryos. In contrast, embryos in the blastocyst stage are more robust. Therefore, the probability of establishing ES cells from frozen embryos which are cultured to the blastocyst stage is much higher than that of using 2 to 3 days old fertilized eggs, which are not cultured to blastocyst stage embryo, as discussed in the U.S. Patent by Thomson (U.S. Pat. No. 6,200,806), which is herein incorporated by reference. By establishing ES cells from frozen embryos cultured to the blastocyst stage, considerable time and cost of establishing ES cells can be saved.

A further feature of the present invention is the use of an anti-human lymphcocyte antibody in immunosurgery of an embryo. The inventors of the present invention found that an anti-human lymphocyte antibody, compared with other commonly used antibodies such as anti-human serum antibodies, is much more effective in removing trophectoderm from the blastocyst embryo.

Definitions

The following terms will be defined as provided unless otherwise stated. All other terminology used herein will be defined with respect to its usage in the particular art to which it pertains unless otherwise noted.

The term "embryo" as defined herein means an embryo after fertilization up to the beginning of the third month of pregnancy when organs and organ systems begin to form.

The term "blastocyst embryo" refers to a pre-implantation embryo consisting of a ball or sphere of cells with an outer cell layer, a fluid filled cavity, and the inner cell mass. As will be appreciated by those of skill in the art, such a sphere is not required to be an idealized geometric sphere, but instead a globular formation of cells. Typically, a blastocyst embryo will be an embryo during the time period of about 5 to 6 days after fertilization.

The term "inner cell mass (ICM)" refers to a group of cells found in the mammalian blastocyst that give rise to the embryo and are potentially capable of forming, all tissues, embryonic and extra embryonic, except the trophoblast. Typically, the inner cell mass will be a cluster of cells within the blastocyst from which human ES cells are derived.

The term "cell" as used herein also includes individual cells, cell lines, or cultures derived from individual cells or cell lines. The term "cell line" as used herein refers to ES cells or cells derived from ES cells such as those maintained in an in vitro culture. Typically, a cell or cell line of the invention or used in a method of the invention will be a human cell or a human cell line.

The term "human ES cells" are cells derived from human embryos that exhibit a pluripotent phenotype as defined hereinbelow.

"Pluripotent" refers to a cell or cells that retain the developmental potential to differentiate into a range of differentiated cell types. Preferably, a pluripotent cell will have the potential to differentiate to derivatives of all three embryonic germ layers: endoderm, mesoderm and ectoderm.

The term "medium" means a suitable medium capable of sustaining undifferentiated ES cells. Similarly, a "medium capable of sustaining undifferentiated embryonic stem cells" refers to a composition in which ES cells can proliferate, can maintain normal karyotype, and can remain pluripotent. A variety of such media are known in the art, as described below.

The term "follicular fluid" refers to fluid produced during follicle growth and which supplies nourishment to the oocyte by facilitating transport of nutrients from plasma. Typically, the follicular fluid used in the method of the invention is hFF.

In one aspect, the present invention provides undifferentiated human ES cells capable of proliferation in vitro and a method of producing such cells. The method of producing undifferentiated ES cells includes the steps of thawing a cryopreserved human embryo and culturing at least a portion of the embryo on a medium capable of sustaining undifferentiated embryonic stem cells. A preferred frozen human embryo used for the above thawing step is an embryo that was cryogenically preserved in the blastocyst stage. A blastocyst stage embryco which was cryogenically preserved about 5 to 6 days after in vitro fertilization is most preferred. In the present invention, a human blastocyst embryo that has been cryogenically stored for more than several years can be used. For example, human zygotes (i.e., fertilized eggs or embryos) used in the working examples of the present invention are blastocyst stage embryos which are normally discarded after being stored for more than 4 years after human in vitro fertilization (human IVF-ET) was performed. In general, extra zygotes are cryogenically preserved and stored by infertility clinics for possible subsequent implantation. However, the current policy of many infertility clinics is to discard the cryogenically perserved and stored zygotes after a particular period of time, if no further implantation requests are made by the parents or if there are no further communications from the parents. An important feature of the present invention is taking advantage of such cryopreserved zygotes, which are ordinarily discarded after a particular period of time. The period of time for discarding unneeded zygotes depends on the policy or guidelines of the particular infertility clinic.

In one embodiment of the invention, there is provided a method for thawing a cryopreserved human embryo by a first step of treating the cryopreserved human blastocyst embryo with a first solution comprising follicular fluid, preferably hFF, and cryoprotectant; then a subsequent second step of treating the cryopreserved human blastocyst embryo with a second solution comprising cryoprotectant; where the second solution comprises a decreased concentration of cryoprotectant relative to the first solution; and where the embryo has been cryopreserved in a solution comprising follicular fluid. Preferably, the second solution also comprises human follicular fluid.

In one embodiment of the invention, blastocyst stage embryos about 5–6 day old are exposed to a solution that contains follicular fluid, preferably hFF, and subsequently exposed to a solution that contains a cryoprotectant such as glycerol or sucrose to prevent the embryos from damage and to maintain proper osmotic pressure. In a preferred embodiment, the cryoprotectant solution also contains follicular fluid, preferably hFF. Thereafter, the embryos are frozen and cryogenically stored in liquid nitrogen. After certain period of time, or preferably sometime after several years of storage of frozen eggs, the method of the present invention can be used to establish ES cells from the embryos. For example, the method of the present invention can be used to establish ES cells where the embryo has been cryogenically stored for more than four years.

In another embodiment of the invention, a method for establishing undifferentiated human ES cells comprises the steps of obtaining a population of cryogenically stored human embryos in the blastocyst stage development, thawing one or more of the embryos, and culturing at least a portion of each of the thawed embryos on a medium capable of sustaining undifferentiated ES cells. In this embodiment, a "population" refers to a collection of two or more embryos, particularly where the two or more embryos are in the blastocyst phase. As disclosed herein, a blastocyst embryo has a higher likelihood of success in establishing undifferentiated human ES cells than embryos at earlier stages of development. Thus, the present invention is useful in a process where most or all of the stored embryos are in the blastocyst stage; preferably all of the stored embryos are in the blastocyst stage.

In thawing the human embryo, the cryoprotectant is removed in order to protect the embryos. The present invention features a method that permits efficient removal of cryoprotectant from the cryopreserved embryos by decreasing the concentration of the cryoprotectant in multiple steps and by treating with follicular fluid. In a preferred embodiment, the embryos are maintained in the presence of follicular fluid throughout the process of removing the cryoprotectant. Only the surviving embryos are cultured in a cell culture. This step modifies and improves preexisting techniques, for example, a method by Menezo et al. (1995), and obtains higher stability by efficiently removing cryoprotectant while maintaining proper osmotic pressure.

In thawing frozen fertilized eggs, several methods are available, such as, for example, the method reported by Menezo. Such methods are reported in publications such as Menezo Y. J. R. et al., 1992, *Human Reproduction* 7:101–106; Kaufnmann R. et al., 1995, *Fert. Steril.* 64:1125–1129; Menezo Y. J. R. et al., 1996, Abstract ASRM 52nd Annual Meeting, which are herein incorporated by reference. The present thawing method is very simple, easy and efficient compared to the Menezo method in terms of the number of treatment steps and time. For example, in one embodiment, the present thawing method requires 5 steps and 17 minutes; in contrast, the Menezo method requires 7 steps and a minimum 38 minutes. Reduced treatment steps and time for thawing avoids unnecessary embryo damage from in vitro environment exposure.

In accordance with the present invention, thawing will take place using at least two solutions containing different concentrations of cryoprotectant. Thus, the method of thawing can contain 2 steps, 3 steps, 4 steps, 5 steps, or more. Preferably, the method of thawing will require 5 steps or fewer. As one of skill in the art will appreciate, the number of steps in the thawing method can be optimized according to the desired survival rate of the thawed embryos. The time duration of each step can also vary according to the desired survival rate, and can vary from brief (i.e., less than about 2 minutes) to long (more than about 10 minutes). Preferably, at least one step will last from about 2 to 10 minutes; and more preferably from about 4 to 6 minutes; typically about 5 minutes.

The cryoprotectant used in the thawing method of the invention can be any compound known to inhibit the crystalline formation of water at freezing temperatures, and particularly those compounds that do not significantly decrease the survival rate of the embryo. By "significantly decrease" is meant a decrease by 30% or more in the survival rate, preferably, a decrease by 20% or more in the survival rate. Such cryoprotectants are known in the art and include a variety of compounds such as sugars including sucrose, glucose, and the like; polyols such as polyethylene glycol, and the like; and a variety of organics such as ethylene glycol, methyl pentanediol, glycerol and the like. The concentration of cryoprotectant used will in part depend on method used in freezing the embrycos. For example, if a slow freezing method is performed, a relatively lower amount of cryoprotectant is used; accordingly, a correspondingly low amount of cryoprotectant would generally be used in thawing the embryos. The concentration of cryoprotectant to be used in the thawing method may be greater if a freezing method involves a relatively greater amount of cryoprotectant. Typically, the cryoprotectant will be about 10 to 50%, depending on the freezing methods used in the cryopreservation of embryos. In the present invention, preferably, a cryoprotectant in the thawing step will be about 30% or less, more preferably about 20% or less, most preferably about 10% or less. For example, glycerol can be used at concentrations such as 9%, and sucrose can be used at 0.4 M (about 14%).

General methods for slow freezing and fast freezing of embryos are known in the art. See, e.g., Rall, W. F., et al. (1985) *Nature* 313:573–575 (ice-free cryopreservation of mouse embryos by vitrification); Gordts, S., et al. (1990) *Fertility Sterility* 53(3):469–472 (survival and pregnancy outcome after ultrarapid freezing of human embryos);

Fahning, M. L., et al. (1992) *Cryobiology* 29:1–18 (status of cryopreservation of embryos from domestic animals); and Abbeel van den, E. et al. (1997) *Human Reproduction* 12(7):1554–1560 (a randomized comparison of the cryopreservation of one-cell human embryos with a slow controlled-rate cooling procedure or a rapid cooling procedure by direct plunging into liquid nitrogen). Thus, one skilled in the art will be able to modify the methods known in the art according to the teachings of the present invention to arrive at improve methods for freezing and thawing, embryos, and improved methods for establishing undifferentiated human ES cells.

Successive cryoprotectant solutions will typically have decreasing amounts of cryoprotectant. For example, glycerol-containing solutions can decrease in concentration by about 2% per successive solution; or sucrose-containing solutions can decrease in concentrations can decrease by about 0.2 M (about 7%) per successive solution. Beyond from the aforementioned examples, any of a variety of additional possibilities exist and can be determined by one skilled in the art.

Multiple cyroprotectants can also be used in a single solution. For example, a solution can contain both glycerol and sucrose. Typically the combined concentrations of the cryoprotectant will not exceed about 30%. In a preferred embodiment, the solution will contain about 5% glycerol and about 0.4 M sucrose. Decreasing concentrations in successive solutions can be of only one cryoprotectant, two or more cryoprotectants, or all cryoprotectants.

In a preferred embodiment, the present invention features use of hFF in thawing frozen fertilized eggs or embryos. The hFF contains essential nutrients and/or environmental conditions for human embryos or fertilized eggs to grow, and it also includes growth and inhibitory factors necessary for embryo survival. Thus, using hFF during the thawing process provides advantages of enhanced embryo survival during the further steps of culturing of the embryos, for example in culturing the embryos to establish ES cells.

In a preferred embodiment, the method for thawing a cryopreserved human embryo includes two or more solutions comprising hFF and cryoprotectant. Preferably, the two or more solutions comprises about 15–25 vol % of hFF.

In another embodiment of the invention, the thawing of the human embryo includes the successive use of three solutions comprising about 4–6 vol % glycerol, about 2–4 vol % glycerol, and about 0.1–2 vol % glycerol, respectively, in addition to each solution also containing hFF. Preferably, at least one or more successive steps are carried out for about 4–6 minutes. The treated embryos can then be further washed with one or more solutions of hFF, which preferably comprise 15–25 vol % of hFF.

In the process of forming ES cells from an embryo, the thawed human embryo is subjected to enzymatic digestion to remove the zona pellucida or a portion thereof. Any protein enzyme may be used to digest the zona pellucida or portion thereof from the blastocyst. A variety of methods and enzymes are known in the art to be useful for such a digestion step, including, for example, pronase and acid Tyrodes solution. Preferably, pronase is used. For digestion of zona pellucida, pronase is used for a period sufficient to remove the zona pellucida, as is readily determined by those skilled in the art. The enzyme-treated embryo is further incubated to dissolve the zona pellucida and to remove pronase toxicity. Removal of the zona pellucida exposes the trophectoderm and the inner cell mass (ICM).

In accordance with the method of the invention, the trophectoderm is separated from the ICM, preferably in a process where the embryo is subjected to immunosurgery. In a particular embodiment of the invention, a novel method of immunosurgery is provided. Specifically, the use of anti-human lymphocyte antibodies (hereinafter "AHLS") is another characteristic feature of the present invention for removing the trophectoderm. Thus, to effectively establish human ES cells derived from frozen-thawed blastocyst stage embryo, AHLS can be used in the immunosurgery process.

Before the invention, anti-human serum antibody has been generally used to remove the trophectoderm. However, the inventors of the present invention realized that trophectoderm from the ICM cannot be completely removed by the anti-human serum antibody. Establishment of undifferentiated ES cells from ICM is dependent upon the complete removal of trophectoderm from the ICM. Thus, use of AHLS in accordance with the present invention increases the efficiency of establishing undifferentiated ES cells from the ICM.

While not intending to be limited by the following theory, it is thought that AHLS is more effective than anti-human serum antibody based on the characteristics of lymphocytes. Lymphocytes are cells with antigen specificity which are preprogrammed to react only with specific antigens. Lymphocytes have anchorage independent cell characteristics which are similar to embryonic cells. Thus, both cell types have similar cell surface antigens. Using AHLS, higher antigen-antibody reactions can be induced on embryos. Thus, the present invention represents a different way of digesting trophectoderm using AHLS, which is found to be much more efficient at dislodging trophectoderm in immunosurgery than other available antibodies. Therefore, the AHLS is specially designed for immunosurgery to selectively obtain the inner cell mass (ICM) in the present invention.

As will be appreciated by those skilled in the art, AHLS can be obtained from a variety of animals including mouse, rat, goat, and any other animal known to produce antibodies and for which a process for obtaining targeted antibodies is known. For example, AHLS can be obtained by injecting human lymphocytes, which are isolated from human blood and mixed with an immune reinforcing agent or a Freund's reinforcing agent, into a rabbit. Except the fact that human lymphocytes are used as an antigen, the desired antibodies can be obtained from an animal using general methods available in the industry related to the art.

Before immunosurgery, heat-complement-inactivation of AHLS is preferable. Exposure of complement-inactivated AHLS provides fast rupture of embryo. Recommended temperatures in serum inactivation protocols range from about 45° C. to about 62° C. and the time will range from about 15 minutes to about 60 minutes. The most common procedure involves subjecting the serum to a temperature of about 56° C. for about 30 minutes. Appropriate treatment concentrations and time for the antibody and a complement in immunosurgery is very important in establishing ES cells. In conventional immunosurgery, usually about 10% concentration of antibody and about 20% concentration of complement are used, in the present invention, preferably about 2–5% concentration of antibody can be used for about 30 minutes to 1 hour and about 5–12% concentration of a complement can be used for about 40–60 seconds.

Thus, the steps for establishing ES cells include removing the zona pellucida from the thawed embryos and immunosurgery. Thawed embryos are treated with pronase to remove zona pellucida and subsequently incubated for a certain time sufficient to detoxify pronase toxicity. Thereafter, the cultures are exposed to AHLS to induce antigen-antibody reaction and further treated with a complement to completely digest trophectoderm. A complement is obtained from whole serum and the type used is important. Typically, rabbit serum is less preferred due to possible toxicity, and guinea pig serum or rat serum are more preferred. Other complements can be determined by one skilled in the art according to the rate of survival of the ICM after treatment with the complement.

Thus, one embodiment of the present method for establishing human ES cells thus comprises treating the embryo to remove the trophectoderm of the embryo or a portion thereof with AHLS to obtain the ICM of the embryo and culturing at least a portion of the ICM on a medium capable of sustaining undifferentiated ES cells.

The present invention also includes a method for isolating and ICM in accordance with the AHLS immunosurgery method discussed above. Preferably, the method for isolating the ICM further includes use of a human blastocyst embryo which has been cryopreserved and thawed.

The present invention also includes an isolated ICM of a human blastocyst formed using the AHLS immunosurgery method of the present invention discussed above.

Culturing of the ICM can be conducted using any of a variety of methods known in the art, including culturing the ICM on a fibroblast feeder layer. To isolate ES cells from cultures, the conditions for culturing should not induce differentiation and should maintain the cells in a proliferation state. For that purpose, several differentiation inhibitory factors can be additionally added. For example, mouse embryonic fibroblast (MEF) cells can be used as a feeder layer for a culture of ES cells to help maintain them as pluripotent stem cells. The inhibition of differentiation of ES cells provided by the MEF feeders appears to be due to their production of leukemia inhibitory factor (LIF) (Williams et al., 1988). MEF cells can be directly isolated from mouse embryos (embryonic day 14 to 16) or supplied as ready-made products (STO cells). Additionally, it can be preferable to add LIF in addition to STO cells for culturing of ICM. STO cells (#CRL-1503) can be purchased from ATCC (American Type Culture Collection, U.S.A.). STO cells are subcultured every two days. It can be desirable to make the recovered cells in droplet after treating with mitomycin-C to inactivate mitosis of feeder cells.

Isolated ICM masses can be plated and grown in culture conditions suitable for human stem cells. Proliferation in vitro may include cultivation of the cells for prolonged periods. The cells are substantially maintained in an undifferentiated state. Preferably the cells are maintained under conditions that do not induce cell death or extra-embryonic differentiation. Also preferably, they are capable of maintaining an undifferentiated state when cultured on a fibroblast feeder layer preferably under non-differentiating conditions. Any medium known in the art as capable of supporting ES cells can be used. For example, a medium for maintaining undifferentiated ES cells can consist of 80% Dulbecco's modified Eagle's medium (DMEM, no sodium pyruvate, high glucose formulation) supplemented with 20% fetal bovine serum (FBS), 1 mM glutamine, 0.1 mM β-mercaptoethanol, 1% ribonucleosides, 1% nonessential amino acids and 0.1% human LIF (2000 units/ml). Seven to ten days after initial plating, ICM derived outgrowth can be dissociated mechanically and re-plated in a fresh feeder layer. The resulting enlarged colony can be mechanically dissociated and chopped into clumps of 50~100 cells, about every seven days.

In a preferred embodiment, the cells have the potential to differentiate in vitro, when subjected to differentiating conditions. Most preferably, the cells have the capacity to differentiate in vitro into a wide array of somatic lineages.

Undifferentiated ES cells may be identified by characteristic morphological observations. Identification of such characteristics can be done by any of a variety of methods known in the art. Methods such as inspection of morphology using a microscope or measurement of alkaline phosphatase activity can be used. Morphological characteristics of ES cells are well known in the art, as exemplified in reports such as Thomson et al. *Science* 282:1145–1147; Reubinoff et al. (2000) *Nature* 18:399–404; and Gearhart et al., WO 98/43679, each of which are herein incorporated by reference. Thomson and Gearhart reported that successful primate ES cell lines have normal karyotypes, and several morphological characteristics such as high levels of intracellular alkaline phosphatase (AP) and presentation of specific cell surface glycolipids and glycoproteins are characteristic of, but not specific for, pluripotent stem cells. Other important characteristics include growth as multicellular colonies, normal and stable karyotypes, the ability to be continuously passaged, and the capability to differentiate into cells derived from all three embryonic germ layers. "Normal karyotype" means that the chromosomal constitution of a cell in terms of the number, size and morphology of the chromosomes at metaphase has normal characteristics of the species.

Figure 13:
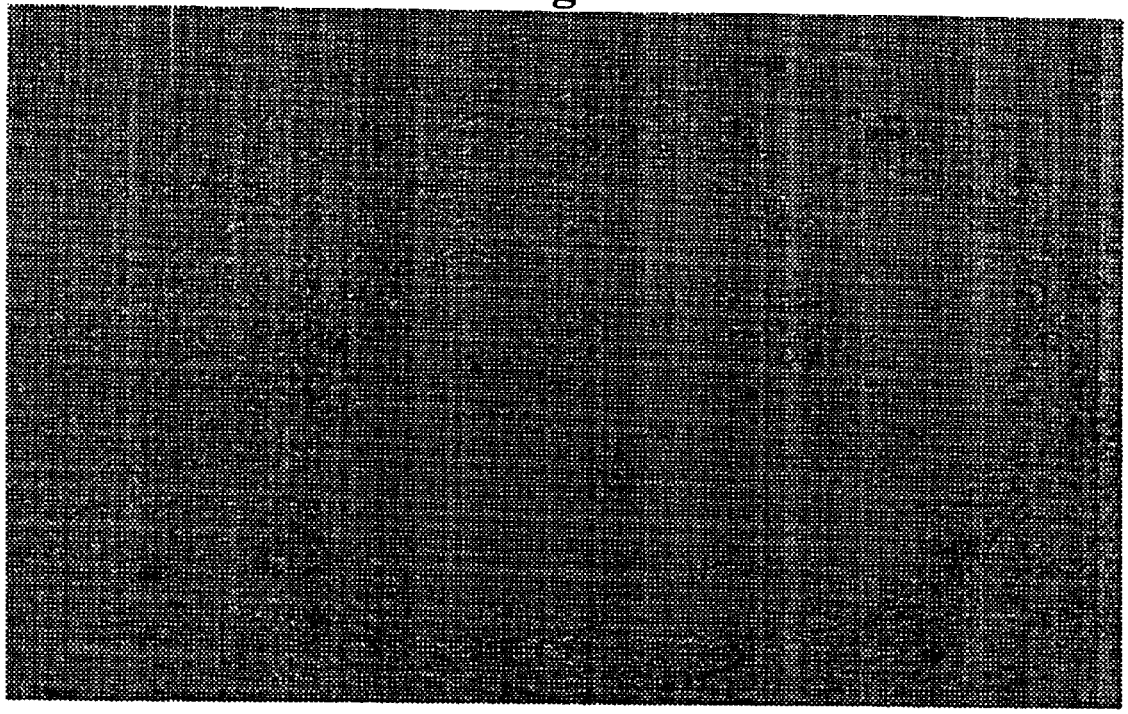
FIG. 13 is a microscopic photograph (X80) showing unstained differentiated cells by alkaline phosphatase activity.
Figure 14:
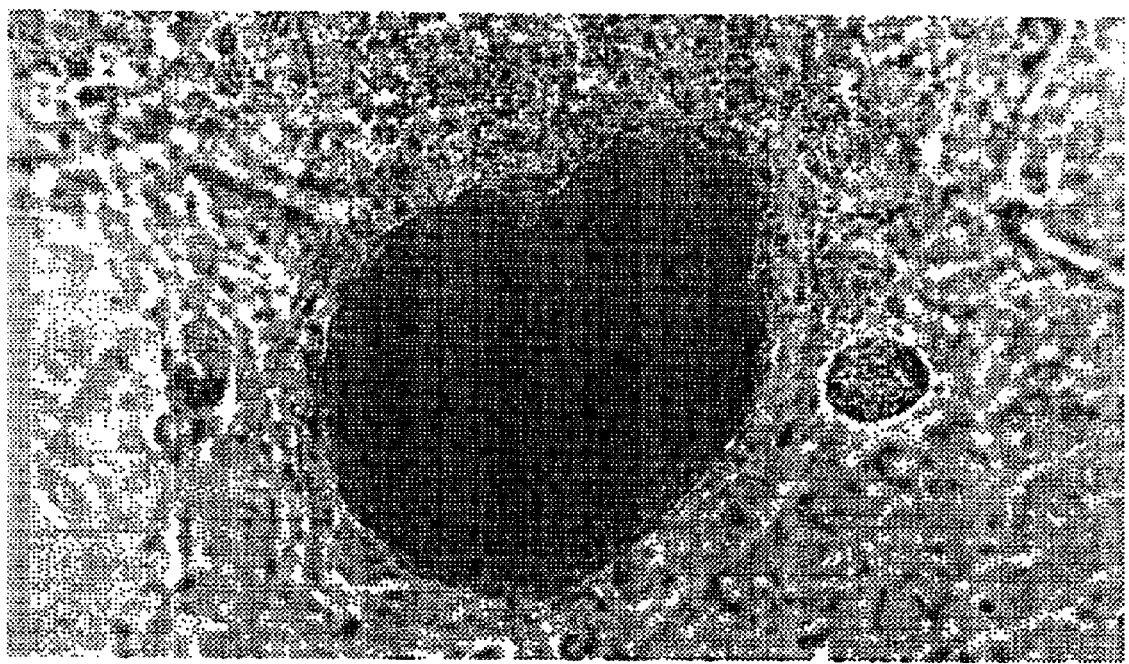
FIG. 14 (X300) shows stained human ES cells by alkaline phosphatase activity.
Figure 15:
FIG. 15 is a microscopic photograph (X40) showing a colony of ES cells differentiating to cardiac myocytes.
Figure 16:
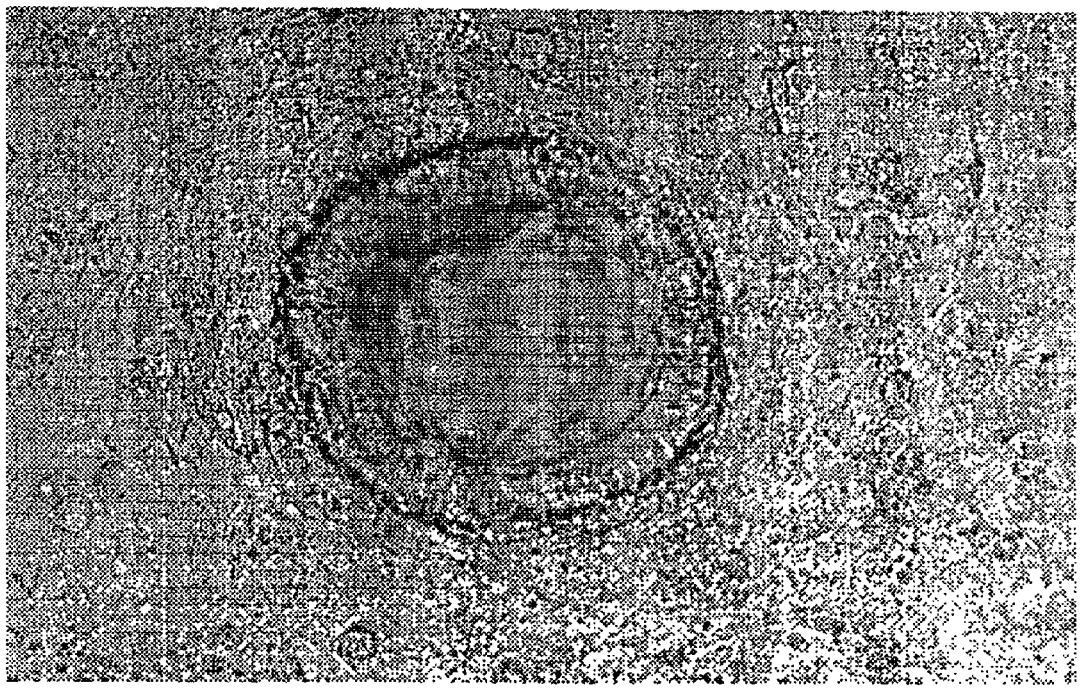
FIG. 16 is a microscopic photograph (X60) illustrating formation of cardiac myocytes according to the method of the present invention.

For more accurate identification of ES cells, it would be more desirable to measure alkaline phosphatase activity in connection with morphological studies. This method permits identification of ES cells by observing the degree of staining. Only the undifferentiated ES cells are stained and differentiated cells are not stained. FIG. 13 shows the unstained differentiated cells and FIG. 14 illustrates stained ES cells.

Figure 27:
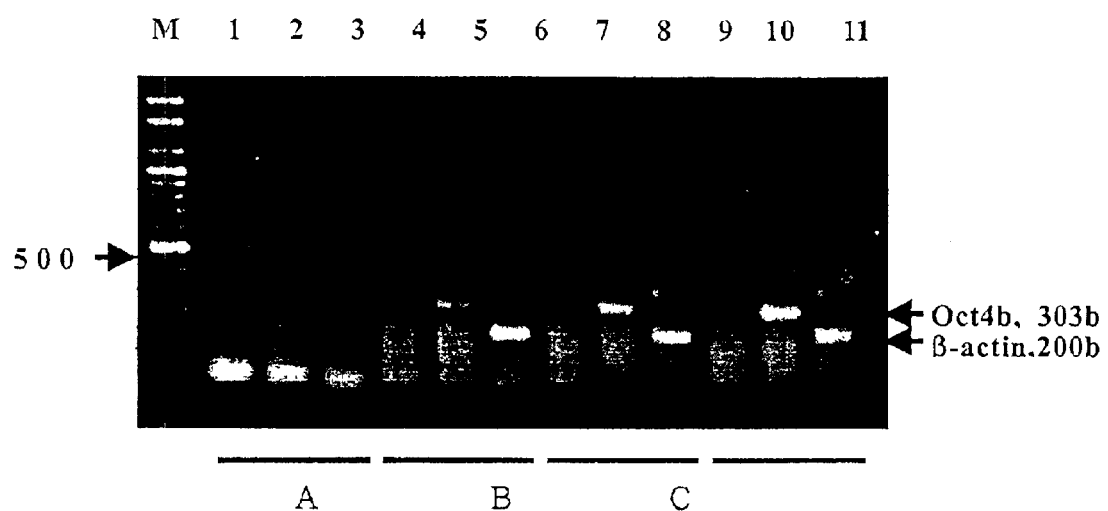
FIG. 27 shows results of electrophoresis for comparing the expression levels of Oct-4 in an embryoid body and a colony of ES cells.
Figure 28:
FIG. 28 shows results of electrophoresis for comparing the expression levels of Oct-4b in ES cells and a colony of differentiated ES cells.

Differential expression of Oct-4 may also be used to identify undifferentiated embryonic stem cells from differentiated cells. Oct-4 is strongly expressed in early embryo, gonad and ES, which exists Oct-4a and Oct-4b by alternative splicing. Oct-4b is expressed stronger than Oct-4a in ES cells (FIG. 27). In addition, Oct-4b is expressed in colonies of ES cells (B, C and D; lanes 4 to 11)(FIG. 27), but neither in embryoid body (EB)(A; lanes 1 to 3)(FIG. 27) nor in differentiated colony (FIG. 28). FIG. 27 shows the electrophoretic results indicating different expression level of Oct-4 in embryoid body (EB) and ES cell colonies. Lanes A in FIG. 27 represent embryoid body and lanes B to D represent ES cells. FIG. 28 shows the electrophoretic results illustrating different expression level of Oct-4 in ES cells (S1, S2) and differentiated ES colony (D1, D2). As shown in FIG. 28, Oct-4b is not expressed in differentiated ES cells while Oct-4b is expressed in undifferentiated ES cells. Therefore, expression of the marker, Oct-4, will be a strong indicator for the presence of undifferentiated ES cells.

Differentiation of ES cells into specific cells can be induced by various methods. In vitro differentiation of ES cells occurs when the cells are allowed to aggregate in suspension culture in the absence of STO feeders and LIF. ES cell aggregates differentiate further to form embryoid bodies containing various cell types including cardiac myocytes, neurons and others. Also, ES cells grown for extended periods at high density without renewal of a feeder layer form aggregates and vesicular structures within which various types of differentiated cells are found. Without growth factors, cells can spontaneously differentiate into many different types of colonies, whereas the addition of growth factors can produce more mature cell morphologies. Growth factor-treated cultures are more homogeneous, and up to half of the culture can contain one or two cell types (muscle-like syncitiums in the activin-A-treated cells, neuronal-like cells in the RA-treated culture and fibroblast-like cells in the cultures treated with BMP-4, etc.). Also, pluripotent stem cells express a wide range of growth factor receptors, and multiple human cell types can be enriched in vitro by specific factors (Schuldiner et al., 2000).

Effective preservation of ES cells is very important as it allows for continued storage of the cells for future usage. Methods which are commonly used for cryopreservation of cell lines can be used. But, methods which are efficient for cryopreservation of embryos are most appropriate for this purpose. In accordance with the present invention, colonies can be ultra-rapidly frozen using ES culture medium with added 10% DMSO. In one embodiment it can be important that the cells be cooled slowly, to prevent the formation of ice-crystals within the cells. For example, cells can be frozen at −20° C. for 1 hour, and then transferred to a −70° C. area overnight; then the next day, the cells can be transferred into liquid nitrogen.

Much attention recently has been devoted to the potential applications of stem cells in biology and medicine. The properties of pluripotentiality and immortality are unique to ES cells and enable investigators to approach many issues in human biology and medicine for the first time. ES cells potentially can address the shortage of donor tissue for use in transplantation procedures, particularly where no alternative culture system can support growth of the required committed stem cell. ES cells have many other far reaching applications in human medicine, in areas such as embryological research, functional genomics, identification of novel growth factors, drug discovery, and toxicology.

The present invention will now be described in more detail through the following practical examples, which are not intended to limit the scope of the present invention.

This invention is not limited to the cells, compositions, reagents, methods, or uses herein below described, since such cells, compositions, reagents, methods, or uses may, of course, vary. The terminology used herein is for the purpose of describing particular embodiment only, and the terminology used herein is not intended to limit the scope of the present invention. Throughout this description, the preferred embodiments and examples shown should be considered as examples only, rather than as limitations to the present invention. All of these will be apparent to one skilled in the art after having the benefit of this disclosure.

EXAMPLES

Example 1

Cryopreservation of Blastocyst Stage Embryos

Five to six day old blastocyst stage embryos from extra fertilized oocytes, which were obtained from the human IVF-ET program of Maria Hospital, Korea, were exposed to 20% hFF for 10 min and subsequently were treated for 10 minutes with a solution containing 20% hFF and 5vol % glycerol. The embryos were then treated in a solution containing 20% hFF, 9vol % glycerol and 0.2 M Sucrose for 10 minutes. The programmed freezing curve was set −1° C./min from 22° C. to −7° C. using a programmed biologic freezer (Planar Kryo: T.S. Scientific, Perkasie, Pa.). Manual seeding was then performed after a 30-second delay. After seeding, the embryo was cooled slowly from −7° C. to −40° C. at a rate of −0.3° C./min. It was then immersed in liquid nitrogen.

Example 2

Thawing of Frozen Blastocyst Stage Embryos

Figure 2:
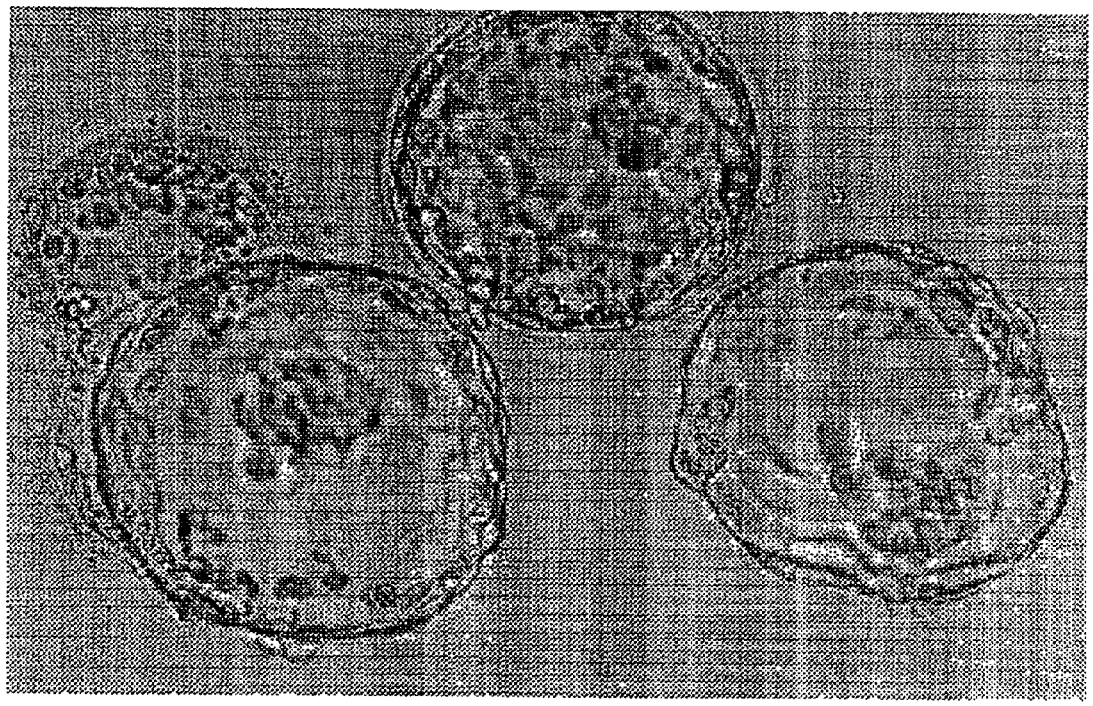
FIG. 2 is a microscopic photograph (X200) showing a re-expanded human blastocyst stage embryo, which was frozen-thawed, after being cultured.

After thawing of the frozen embryos, which were treated and cryogenically kept for more than four years, the thawed embryos were briefly treated with a solution of 20% hFF, 5vol % glycerol and 0.4 M sucrose for recovery, and were subsequently treated with a solution of 20% hFF, 3vol % glycerol and 0.2 M sucrose for 5 minutes. Thereafter, they were treated again in a solution of 20% hFF, 1 vol % glycerol and 0.2 M sucrose for 5 minutes, and following the treatment they were exposed to a solution of 20% hFF and 0.2M sucrose for 2 minutes. Following this, the embryos were treated with a 20% hFF solution for 5 minutes (FIG. 1), and the surviving embryos were cultured in a culture media for 24 hours (FIG. 2).

Example 3

Generation of Rabbit Anti-human Lymphocyte Antibody (AHLS)

Human lymphocytes (>4×10⁸ cells) recovered from Ficoll plaque treatment (Amersham Pharmacia Biotech AB, research grade) were mixed with RIBI adjuvant (R-700, RIBI Immunochem Research, Inc.) or Freund's adjuvant and were injected into a rabbit every two weeks for a total of four times. Blood enclosed AHLS were recovered from heart puncture of the rabbit ten days after the last injection.

Example 4

Isolation of Inner Cell Mass (ICM) by Immunosurgery

Figure 3:
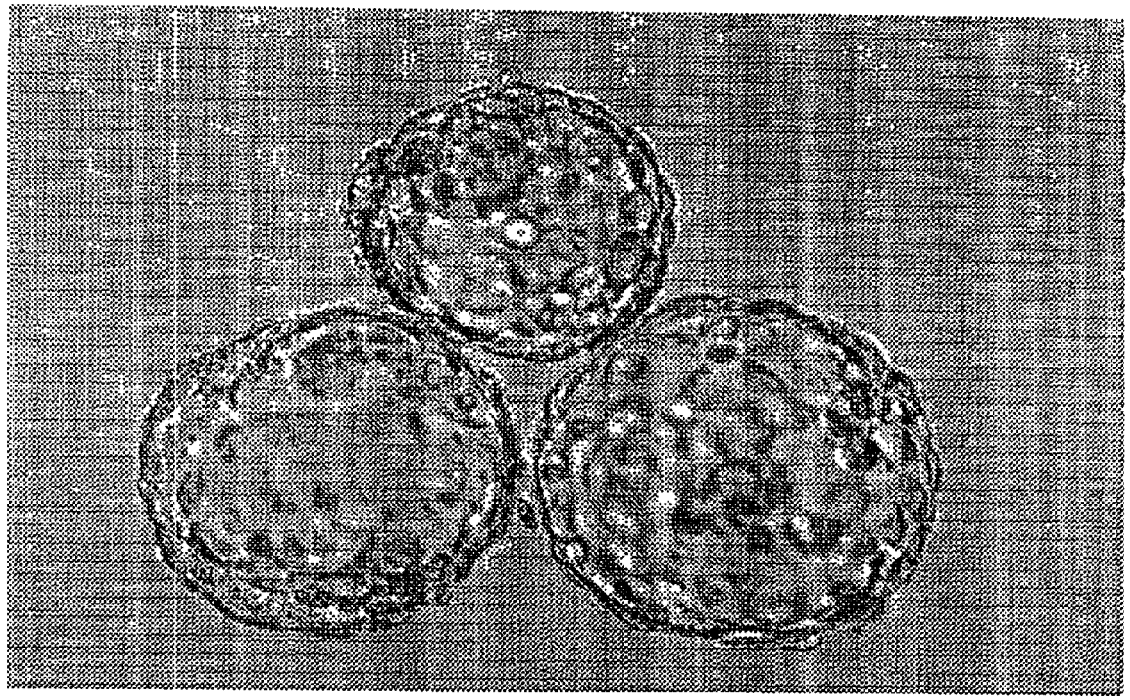
FIG. 3 is a microscopic photograph (X200) capturing a human blastocyst stage embryo with its zona pellucida removed by pronase treatment.
Figure 4:
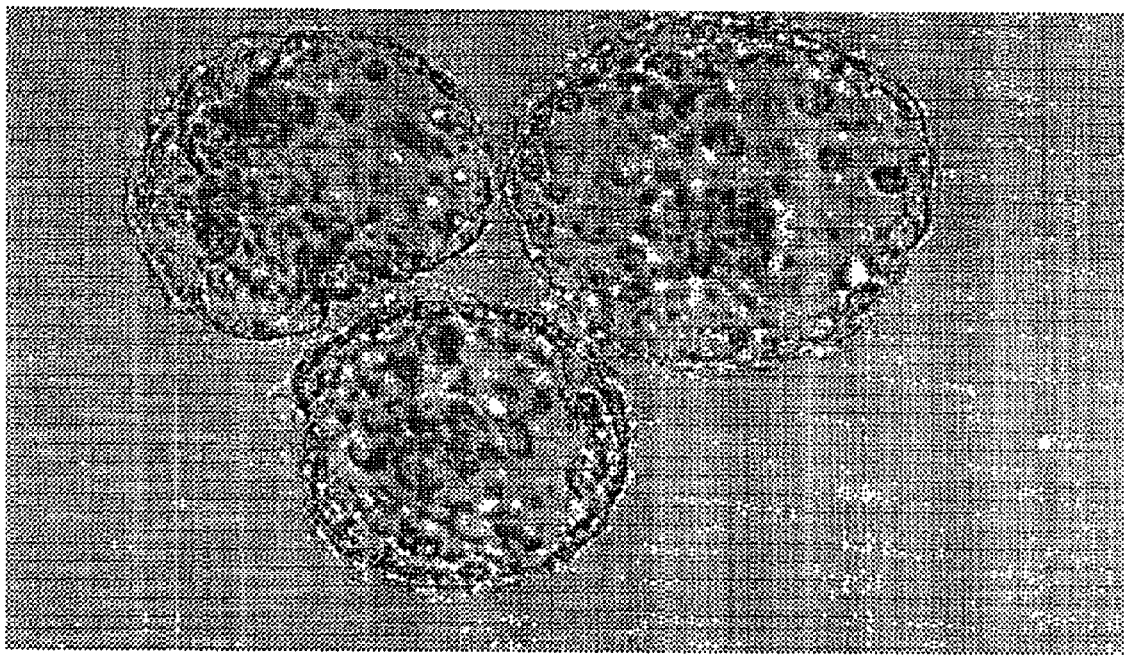
FIG. 4 (X200) shows a human blastocyst stage embryo with its trophectoderm digested away by immunosurgery.

Before immunosurgery, AHLS was heat-complement inactivated at 56° C. for 30 min. The complement was absorbed with agarose, stored at −70° C. and only thawed immediately prior to use. Complement acted on cell parts induced with antigen-antibody reaction and terminated them. A 5% concentration of the antibody was treated for 30 min, and a 10% concentration of a complement was treated for 40–60 sec. After zona pellucida digestion by 0.25% pronase (FIG. 3) in TL-Hepes solution, the ICM was isolated by exposure to 5% rabbit anti-human lymphocyte antibody (AHLS) for 15 minutes and exposure to 10% guinea pig complement for 1 to 2 minutes (FIG. 4).

Example 5

Preparation of STO Cells

STO (mouse embryonic fibroblast, ATCC) cells were prepared to co-culture with the ICM. Frozen STO cells were aerated for 20 seconds and placed in warm water (36.5° C.) until the cells were completely thawed. 9 ml of warm HBSS or STO culture medium were added and mixed together. After centrifugation at 1000 rpm for 10 minutes, supernatant was removed and the precipitate was resuspended in 3 ml of warm 10% FBS added DMEM (Dulbecco's modified eagle medium), and cultured in 25-T culture flask. The resulting culture was subcultured every two days.

Example 6

Generation of Feeder Drop Cells from the Isolated STO Cells

After confirming STO cells to confluency in culture flask, the cells were washed by PBS solution, treated by 10 μg/ml mitomycin C added DMEM for 2.5 hours, then washed three times with PBS solution, and subsequently treated by 1× trypsin-EDTA. The resulting cells were washed by 5 ml warm HBSS solution and centrifugated at 1000 rpm for 5 minutes. After discarding the supernatant, the precipitates were resuspended by 5 ml HBSS solution. After a second centrifugation of the solution at 1000 rpm for 5 minutes, the supernatant was discarded and the precipitate was resuspended in 1 ml of DMEM-LIF solution. Thereafter, portions of the cells were counted by trypan blue (1:1) and hematocytometer chamber and the remainder of the cells were seeded (250,000 cells/ml) in culture plates (Falcon, #3653) after resuspension.

Example 7

ICM Cell Cultivation and Their Sub-culture

Figure 7:
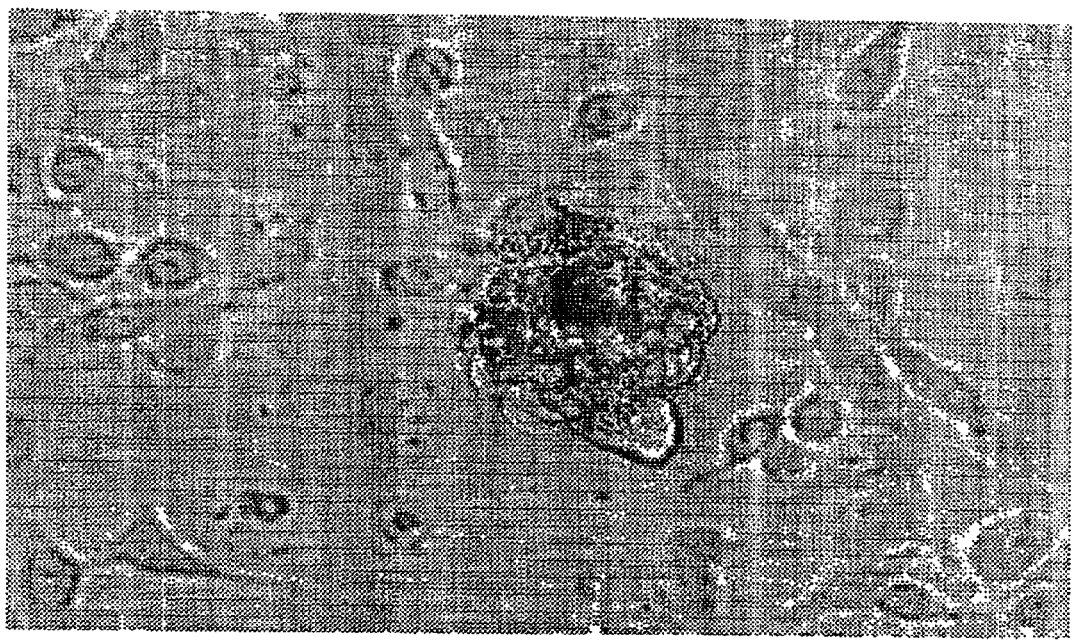
FIG. 7 is a microscopic photograph (X400) of ICM cells, which were placed onto STO cells.
Figure 8:
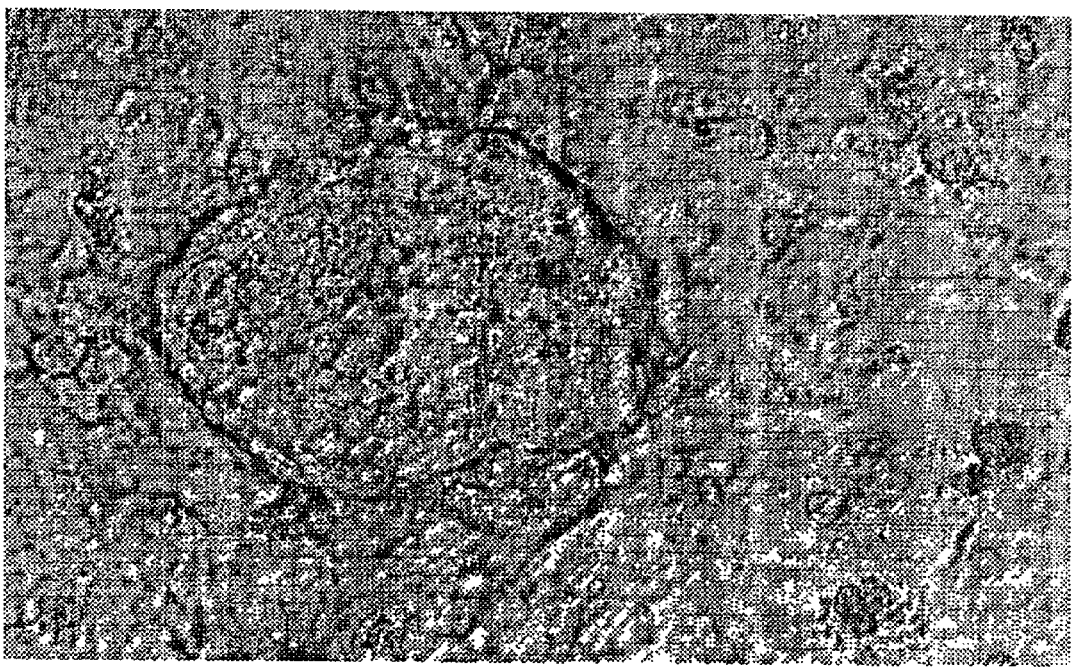
FIG. 8 (X300) depicts ICM colonies that formed after 7 days from initial plating.
Figure 9:
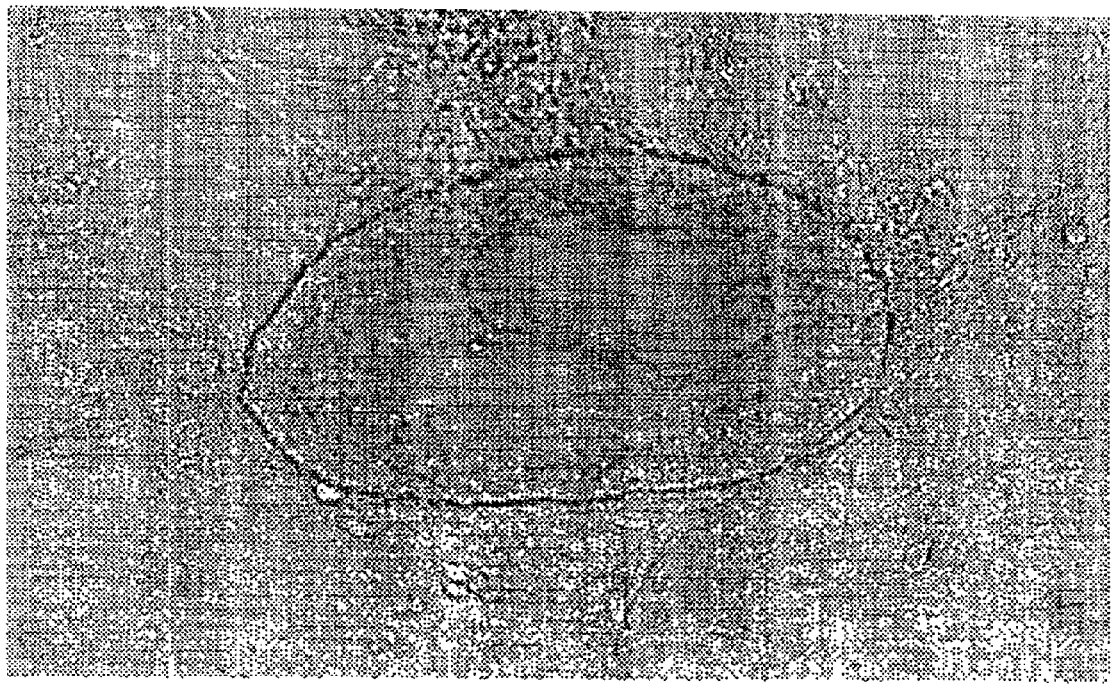
FIG. 9 (X80) shows ICM colonies that formed 13 days after replating the ICM colonies shown in FIG. 8.
Figure 10:
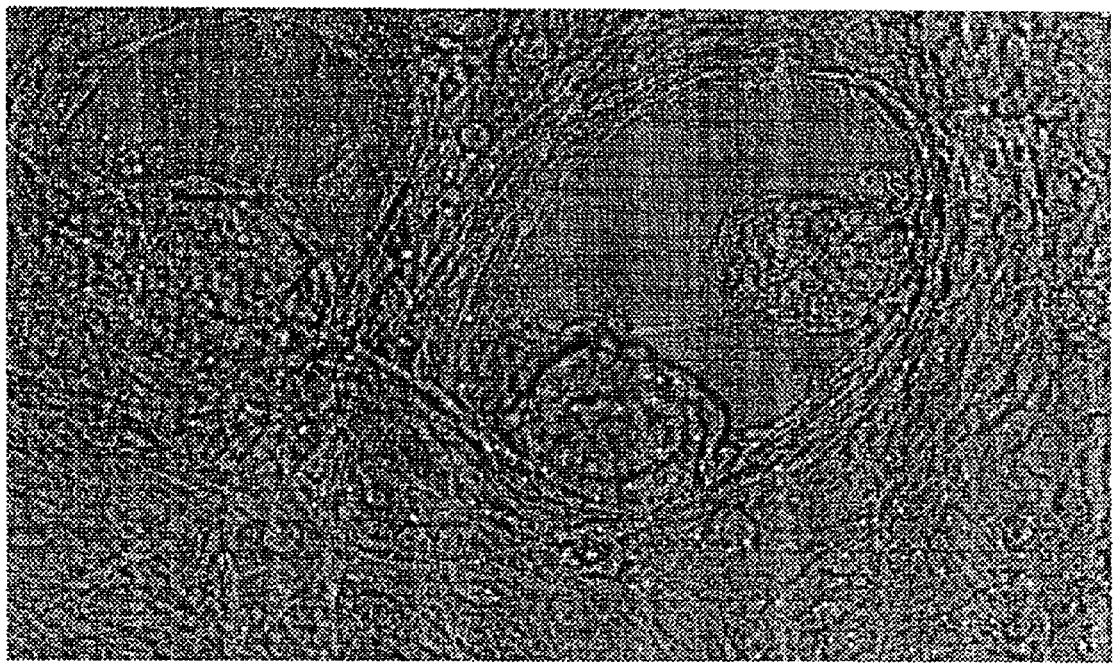
FIG. 10 (X150) shows ICM cells that were mechanically separated and cultured.
Figure 11:
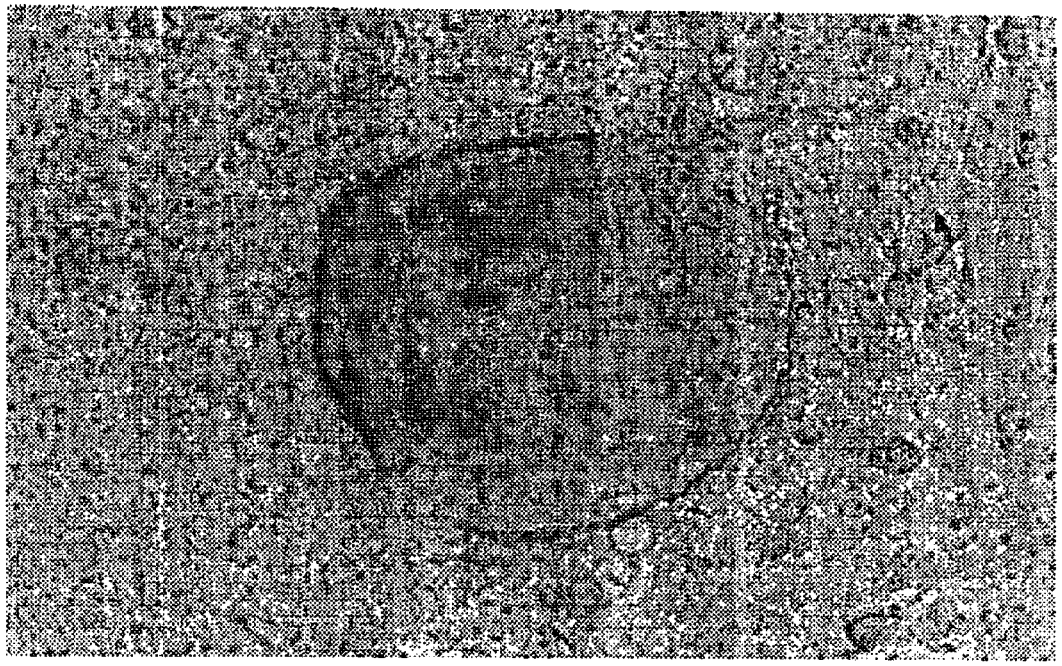
FIG. 11 (X200) shows isolates of a colony of human ES cells, which were cultured for 5 weeks.
Figure 12:
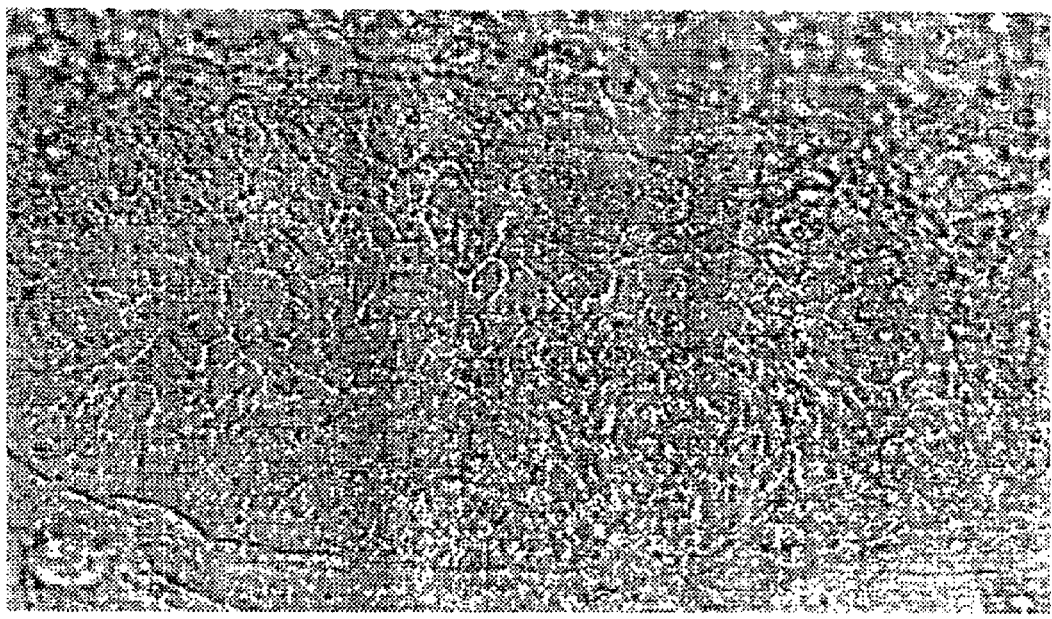
FIG. 12 shows a further magnification (X400) of the colony shown in FIG. 11.

The isolated ICM was placed onto STO cell feeder layer using a micropipette (FIG. 7) and continuously cultured using fresh DMEM containing LIF (2000 units/ml) which was changed daily. The ICM clump that formed was replated on a fresh STO feeder layer and continuously cultured. The ICM clump was divided into several subcolonies by mechanical dissociation and cultured on fresh STO feeder layer approximately every 7 days.

Example 8

ES Cells Characterization

Following the published methods by James Thomson and coworkers (Thomson et al., (1998) *Science* 282:1145–1147) and Benjamin Reubinoff and coworkers (Reubinoff et al., (2000) *Nature* 18:399–404), ES cells were confirmed with morphological observation through a microscope. In addition, ES cells were fixed in 4% formaldehyde for 15 minutes and washed three times by sterile distilled water, and subsequently were stained with Fast Red TR/Naiphthol AS-MX solution (Sigma, St. Louis, Mo.) for 15–30 minutes, and the degree of staining was observed.

As an alternative, monitoring of expression of Oct-4 by RT-PCR was carried out on colonies consisting predominantly of stem cells. mRNA isolated through whole cell extraction and cDNA synthesis was performed by reverse transcription. The following primers were used for PCR amplification: 5'-CCACATCGGCCTGTGTATAT-3' (SEQ ID NO:1, antisense primer for Oct-4a and Oct-4b) and 5'-CTCCTGGAGGGCCAGGAATC-3' (SEQ ID NO:2, sense primer for Oct-4a), 5'-ATGCATGAGTCAGTGAACAG-3' (SEQ ID NO:3, sense primer for Oct-4b). PCR amplification was performed as follows: 1 min at 94° C., 1 min at 55° C., and 1 min at 72° C. up to 35 cycles. PCR products were analyzed on 1% agarose gel and visualized by ethidium bromide staining followed by Biorad image analyzer. Oct-4a and 4b expression was monitored by this method. Table 1 summarizes the results.

TABLE 1

| | |
|---|---|
| Number of thawed blastocyst stage embryos | 6 |
| Number of surviving blastocyst stage embryos after thawing | 5 |
| Number of blastocyst stage embryos targeted by immunosurgery | 4 |
| Number of ICM plated on medium | 4 |
| Number of ICM fixed on medium | 2 |
| Number of colonies formed from the ICM | 2 |
| Number of colonies formed after subculture | 2 |

Figure 30:
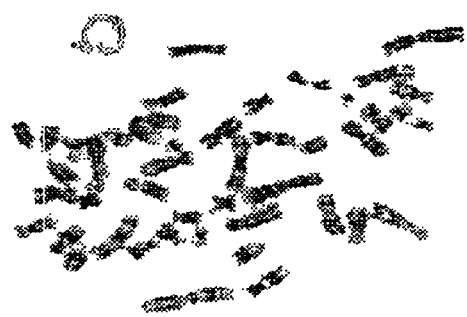
FIG. 30 is a metaphase spread.
Figure 31:
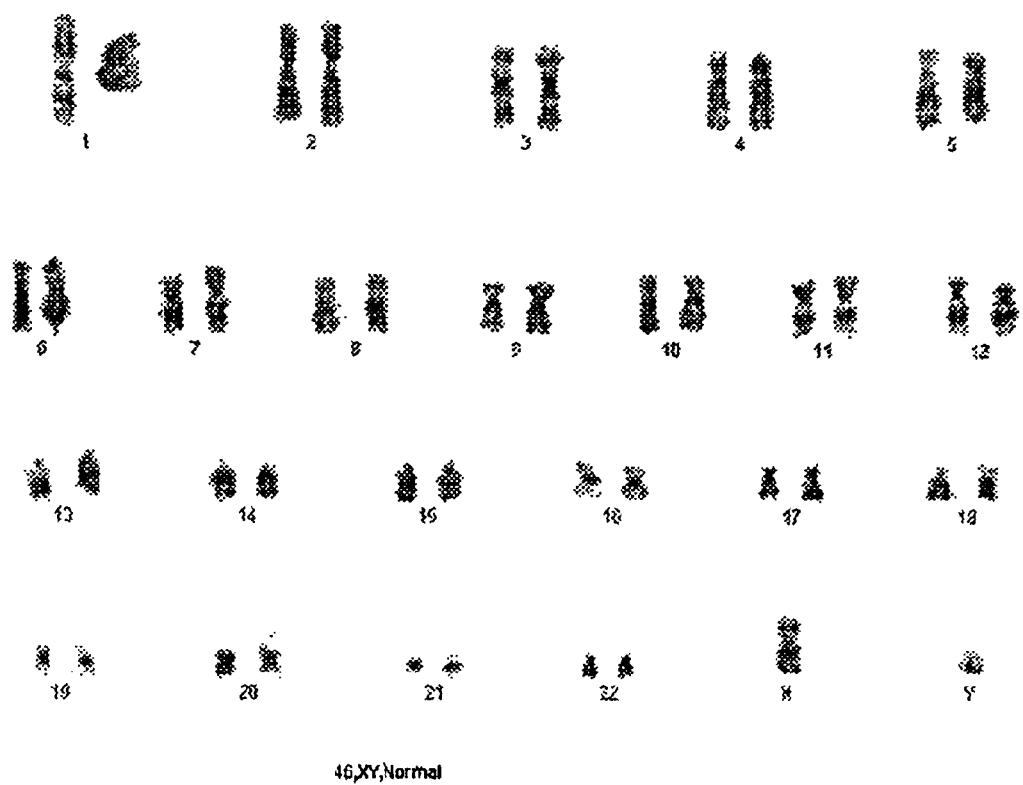
FIG. 31 is karyotype of human ES cell line.

As shown in Table 1, four blastocyst stage embryos were recovered for immunosurgery and two colonies formed from the four ICM. These two colonies were divided into several subcolonies and most of the ICM appeared undifferentiated and propagated during five to six subculturing (45–50 days after immunosurgery). Further, the karyotype of the human frozen-thawed embryo-derived cell cultures was examined. For chromosome analysis, human ES colony at passage 10 to 15 was cultured in a dish without STO feeder layer for 3 to 5 days. Colcemid (5%) treated and harvested cells were stained by standard G-banding techniques. Metaphase and karyotyping were analyzed using Cytovision program (Applied Imaging Co.—FIGS. 30 and 31). In addition, alkaline phosphatase activity was demonstrated. Alkaline phosphatase activity was not detected in differentiated colonies (FIG. 13) whereas there was strong alkaline phosphatase activity in undifferentiated colonies (FIG. 14). Furthermore, the expression of Oct-4 confirmed that Oct-4b was expressed in ES cells, and was not expressed in embryoid body, which is a differentiated cell type, nor in differentiated colonies (FIGS. 27 and 28).

Example 9

Differentiation of Human ES Cells to Specific Cells

Figure 5:
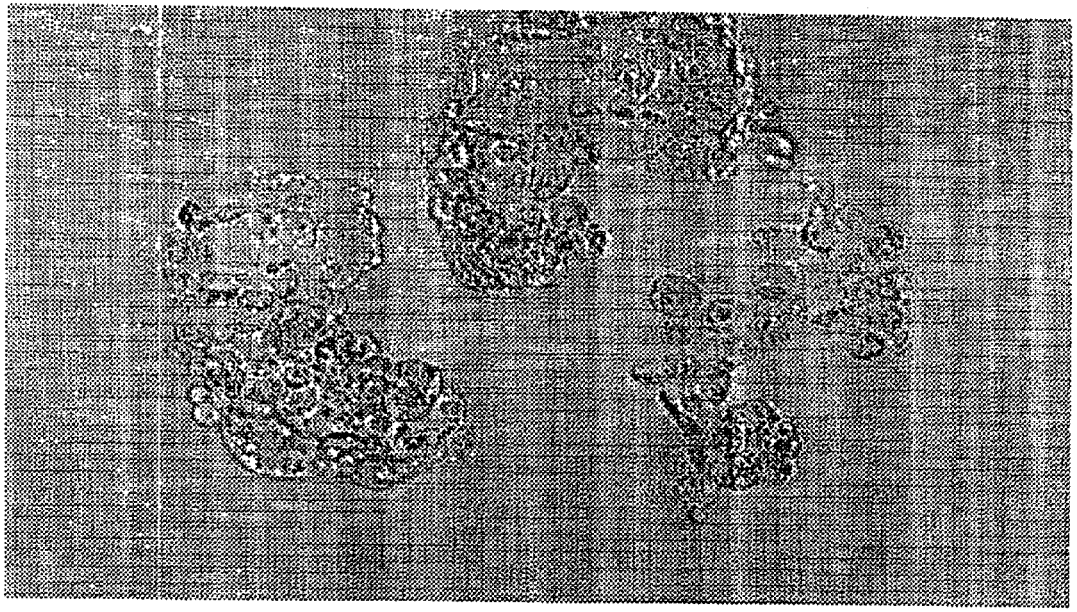
FIGS. 5 and 6 are microscopic photographs (X200) of inner cell mass (ICM) from the remaining blastocyst stage embryo after complete digestion of trophectoderm.
Figure 6:
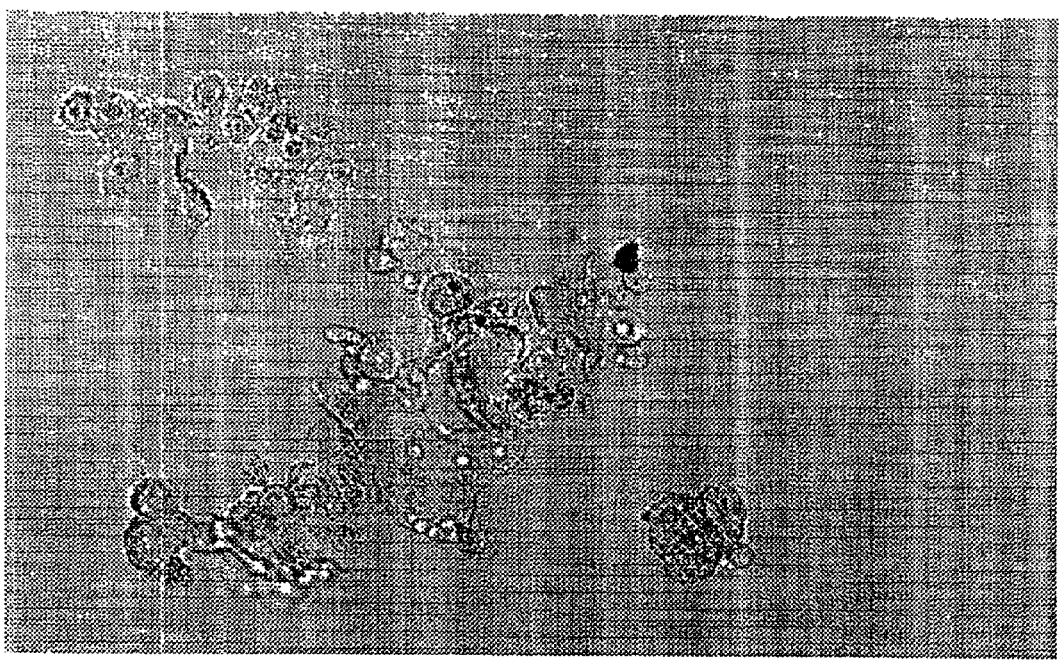

To the ES cells identified, growth factors and basic culture medium (L-glutarnine, non essential amino acids, and 20% FBS) were added to induce differentiation. For the purpose of differentiating to cardiac myocytes, 1 µM retinoic acid (RA) was added to the colonies, which are undergoing differentiation. The results are shown in FIGS. 3 to 5. To direct differentiation to neuronal cells, 1 µM retinoic acid (RA), 10 ng/ml basic fibroblast growth factor (b-FGF), and/or 100 ng/ml nerve growth factor (NGF) were added to embryoid body or differentiating colonies. The culture medium was replaced daily. Moreover, differentiation to muscle cells was confirmed by the conditions set forth for the differentiation to the cardiac myocytes.

Example 10

Identification of Differentiation to Specific Cells

Figure 17:
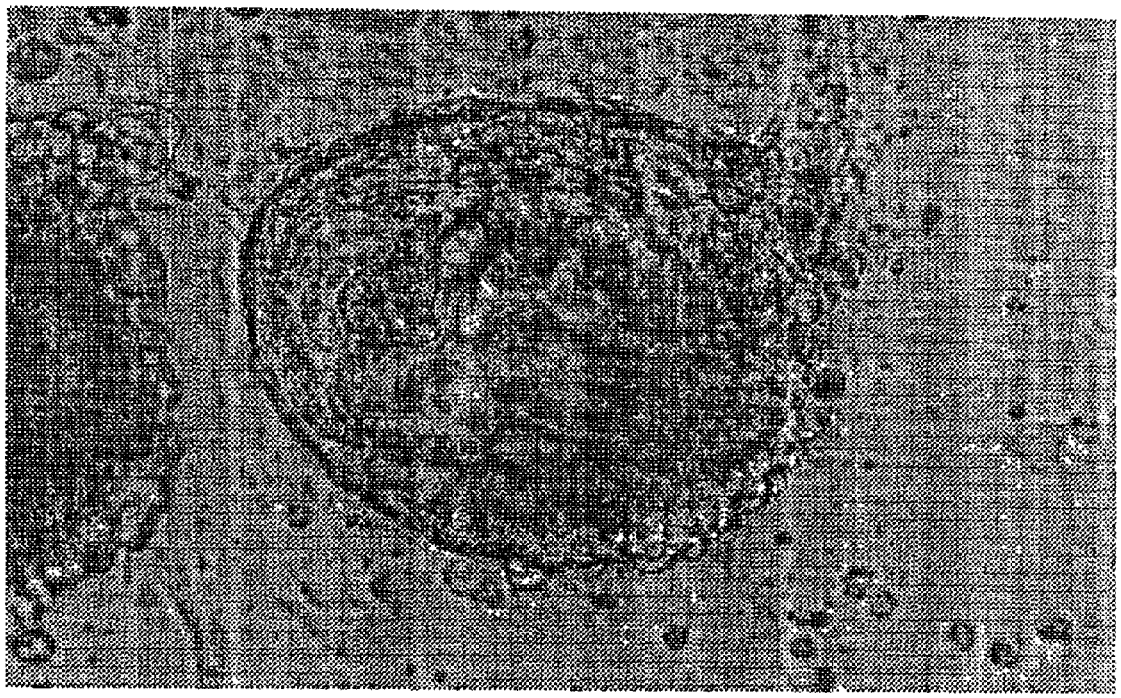
FIG. 17 is a microscopic photograph (X100) of pulsing cardiac myocytes which have been differentiated according to the present invention.
Figure 18:
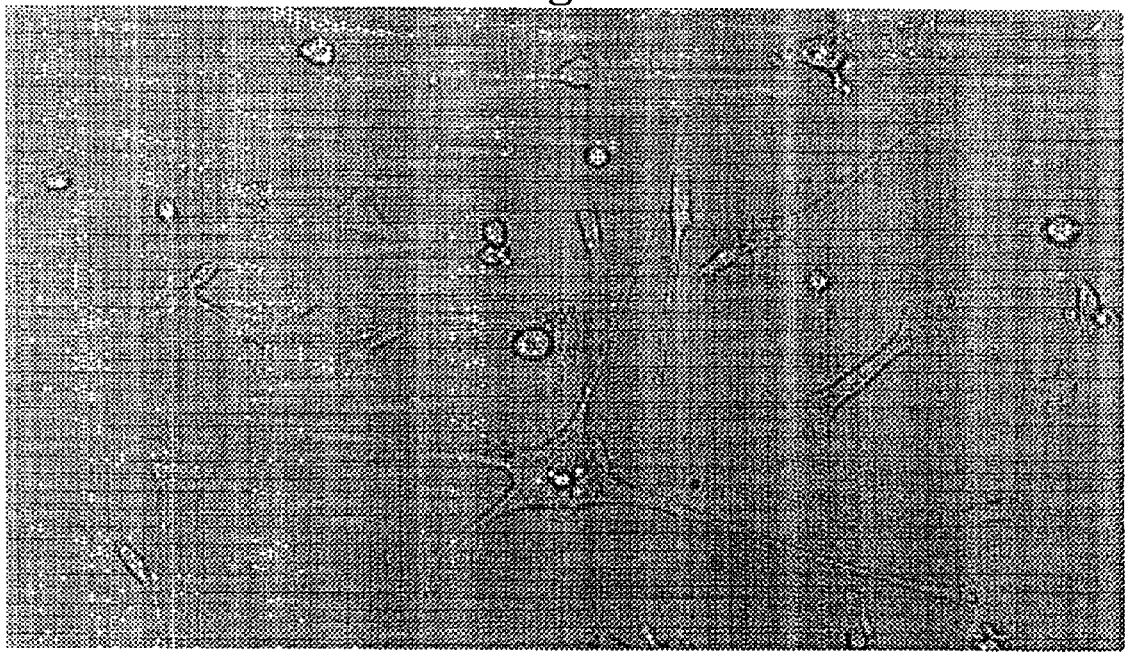
FIG. 18 is a microscopic photograph (X100) of a typical neuron.
Figure 19:
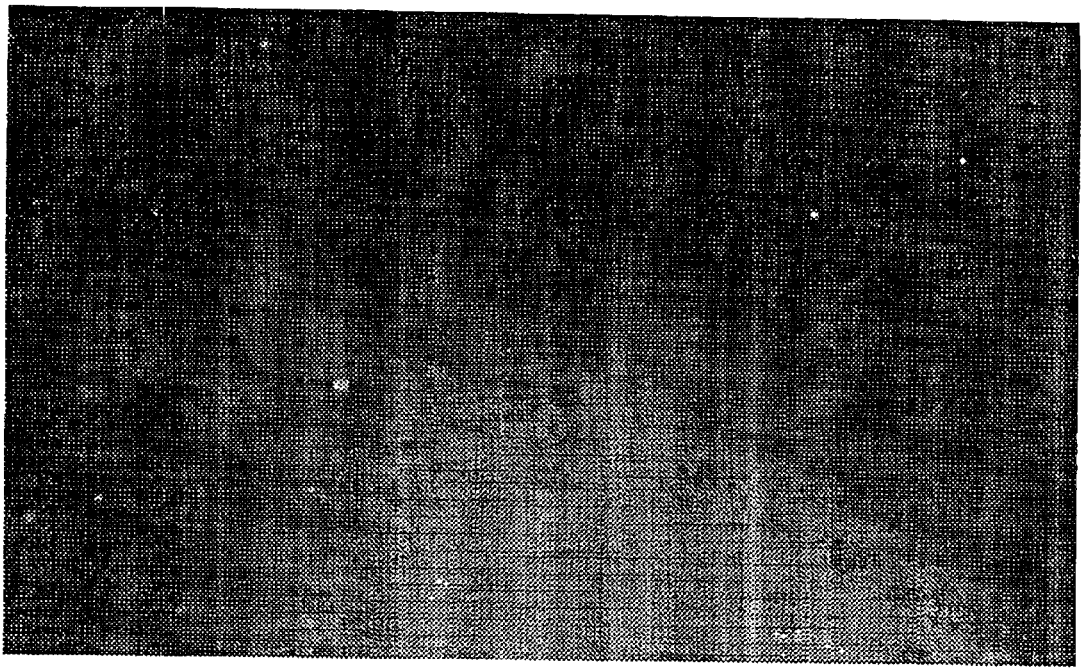
FIG. 19 is a microscopic photograph (X40) of a neuronal cell stained with 200 kDa anti-neurofilament protein.
Figure 20:
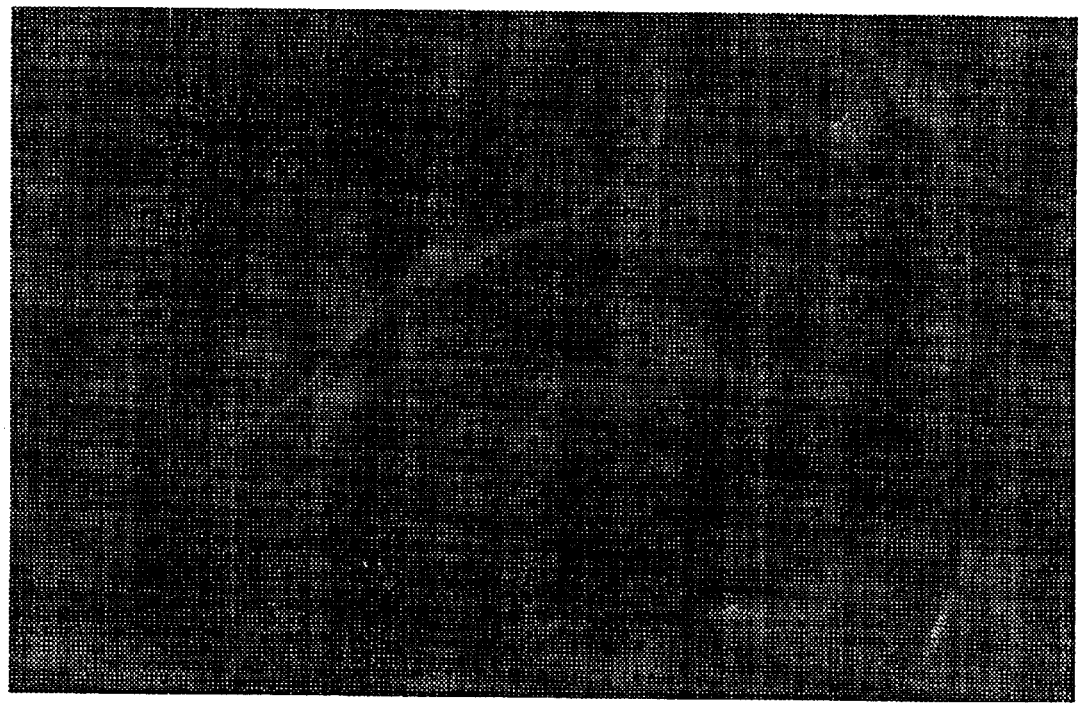
FIG. 20 is a microscopic photograph (X600) of a neuronal cell stained with microtubule associated protein 2.
Figure 21:
FIG. 21 is a microscopic photograph (X600) showing a neuronal cell stained with anti-β-tubulin.
Figure 22:
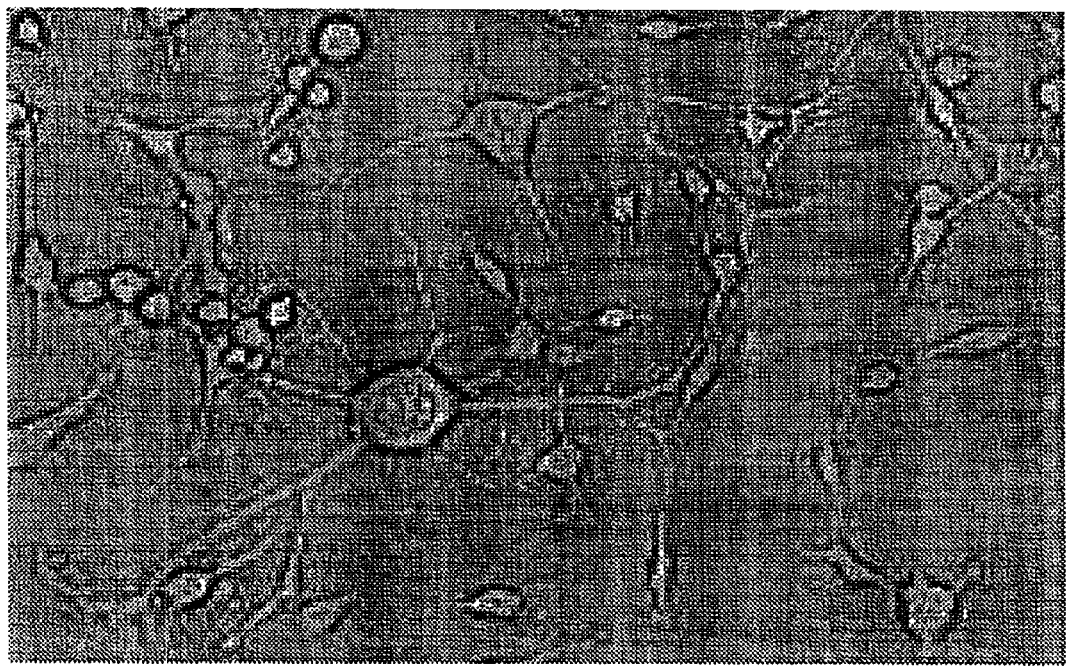
FIG. 22 is a microscopic photograph (X100) of typical glial cells.
Figure 23:
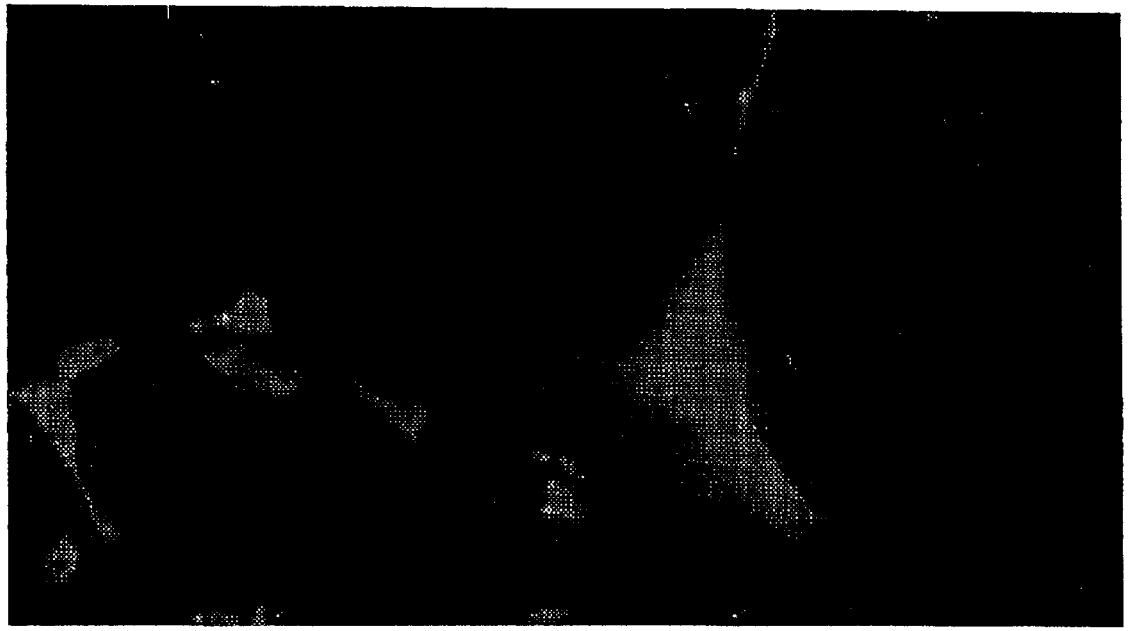
FIG. 23 is a microscopic photograph (X100) of glial cells stained with anti-glial fibrillary acid protein.
Figure 24:
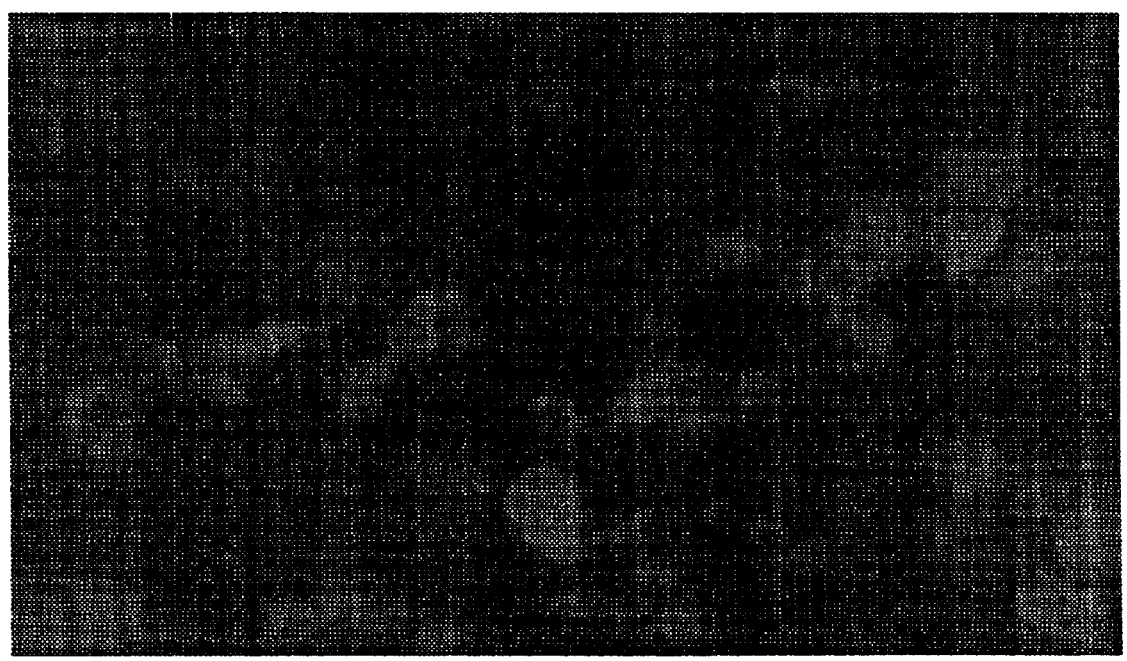
FIG. 24 is a microscopic photograph (X200) showing glial cells stained with anti-galactocelebrocide.
Figure 25:
FIGS. 25 and 26 are microscopic photographs (X400) of muscle cells stained with anti-muscle specific actin.
Figure 26:
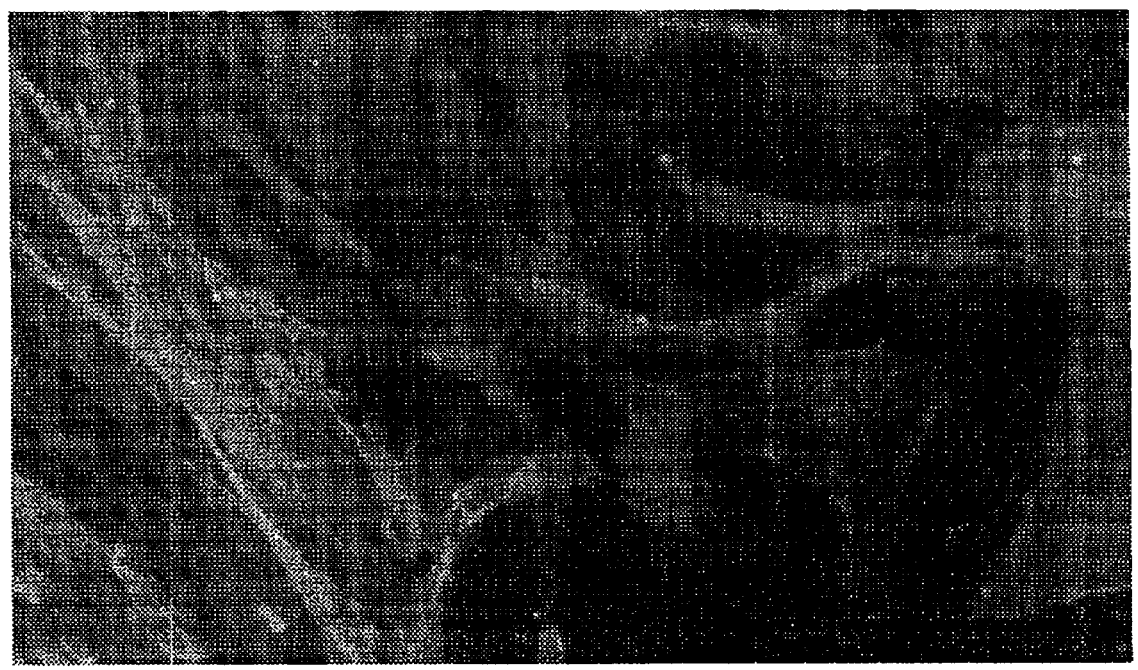

Differentiation to specific cells from the ES cells was first identified by their characteristic morphological features. In the case of differentiation to cardiac myocytes, as shown in FIG. 17, morphological features showing regular routine heart-beat was observed. Differentiated cells were further identified by immunochemical assays. To identify neuronal cells, specific monoclonal antibodies were used to detect 200 kDa neurofilament protein (NF200, Sigma), microfilament adhesion protein2 (MAP2, Sigma), and β-tubulin (Sigma). FIGS. 19 to 21 illustrate the results. To identify glial cells, polyclonal antibodies were used to detect glial fibrillary acid protein (GFAP) and Galactocelebroside (GalC) and the results are shown in FIGS. 22 to 24. Muscle cells were identified with a monoclonal antibody that has specificity to muscle specific action (Sigma) (FIGS. 25 and 26). Secondary antibody complemented with FITC was prepared to detect reaction level to each antibody. All the steps for staining were performed at 4° C. These steps were based on the methods described in the articles by Reubinoff and others.

Example 11

Cryopreservation and Thawing of Human ES Cells

Cryopreservation was attempted to find out whether long-term storage of human ES cells was possible. Cryoprotectant for the cryopreservation of the ES cells was prepared by adding 10% DMSO to the ES cells medium and used after filtration. To reduce toxicity of the cryoprotectant, colonies of ES cells were directly placed into a freezing tube in which the cryoprotectant is contained and were placed at −20° C. for two hours. The frozen cells were stored at −70° C. thereafter for 10 months.

Figure 29:
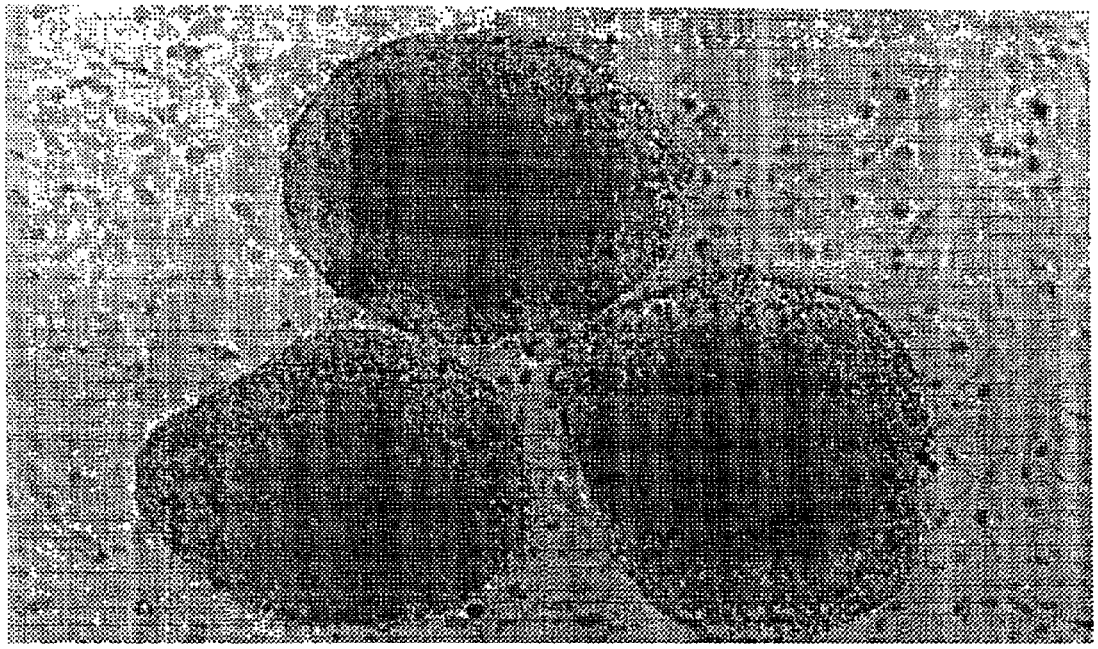
FIG. 29 is a microscopic photograph (X60) of a frozen-thawed human ES cell prepared by the method of the present invention.

The freezing tube was completely thawed at 36° C. in a water bath and the cryoprotectant was removed by placing the contents of the tube into ES cell culture medium. Isolated ES cell clumps were immediately placed in the culture container and viability was investigated. ES cells prepared by the present invention were found to be viable after being freeze-thawed. FIG. 29 shows this result.

Although, the present invention has been described as above, it will be apparent to one skilled in the art that many other variations and modifications are possible after having the benefit of this disclosure. All such variations and modifications are considered within the scope and spirit of this invention.

What is claimed is:

1. A process for making undifferentiated human embryonic stem cells, comprising the steps of:
  (a) thawing a cryopreserved human blastocyst embryo;
  (b) isolating the inner cell mass by a process comprising the step of removing the trophectoderm from said embryo using anti-human lymphocyte antibody; and
  (c) culturing at least a portion of said inner cell mass on a medium capable of sustaining undifferentiated embryonic stem cells, whereby undifferentiated human embryonic stem cells are established.

2. The process of claim 1, wherein said human blastocyst embryo comprises a human embryo that was cryopreserved from about 5 days to about 6 days after fertilization of said embryo.

3. The process of claim 1, wherein said human blastocyst embryo has been cryogenically stored for more than four years.

4. The process of claim 1, wherein said thawing step comprises:
  (a) a first step of treating said cryopreserved human blastocyst embryo with a first solution comprising human follicular fluid and cryoprotectant;
  (b) a subsequent second step of treating said cryopreserved human blastocyst embryo with a second solution comprising human follicular fluid and cryoprotectant; wherein said second solution comprises a decreased concentration of cryoprotectant relative to said first solution.

5. The process of claim 4, wherein said cryoprotectant is selected from the group consisting of sucrose, glycerol and a combination of sucrose and glycerol.

6. The process of claim 4, further comprising a subsequent third step of treating said cryopreserved human blastocyst embryo with a third solution comprising hFF and cryoprotectant; wherein said third solution comprises about 0.1–2 vol % glycerol, said second solution comprises about 2–4 vol % glycerol, and said first solution comprises about 4–6 vol % glycerol.

7. The process of claim 4, wherein at least one of said treating steps is carried out for about 4–6 minutes.

8. The process of claim 4, wherein said first solution and said second solution each comprise about 15–25% human follicular fluid.

9. The process of claim 1, wherein said thawing step consists of:
  (a) a first step of treating said cryopreserved human blastocyst embryo with a first solution comprising human follicular fluid and cryoprotectant;
  (b) a subsequent second step of treating said cryopreserved human blastocyst embryo with a second solution comprising human follicular fluid and cryoprotectant;
  (c) a subsequent third step treating said cryopreserved human blastocyst embryo with a third solution comprising hFF and cryoprotectant;
  (d) a subsequent fourth step of treating said cryopreserved human blastocyst embryo with a fourth solution comprising hFF and cryoprotectant; wherein said fourth solution comprises a decreased concentration of cryoprotectant relative to said third solution, said third solution comprises a decreased concentration of cryoprotectant relative to said second solution, and said second solution comprises a decreased concentration of cryoprotectant relative to said first solution.

10. The process of claim 1, wherein the culturing step is carried out in the presence of mouse embryonic fibroblast STO cells.

11. A process for making undifferentiated human embryonic stem cells comprising the steps of:
   (a) obtaining at least two cryogenically stored human embryos, wherein said at least two embryos consist solely of embryos in the blastocyst phase;
   (b) thawing one or more of said at least two embryos;
   (c) isolating the inner cell mass by a process comprising the step of removing the trophectoderm from said embryo using anti-human lymphocyte antibody; and
   (d) culturing at least a portion of each of said inner cell mass on a medium capable of sustaining undifferentiated embryonic stem cells; whereby undifferentiated human embryonic stem cells are established.

12. The process of claim 11, wherein the culturing step is carried out in the presence of mouse embryonic fibroblast STO cells.

* * * * *